US005532136A

United States Patent [19]
Carlson et al.

[11] Patent Number: 5,532,136
[45] Date of Patent: Jul. 2, 1996

[54] MONOCLONAL ANTIBODY ASSAY AND KIT FOR DETECTING METAL CATIONS IN BODY FLUIDS

[75] Inventors: Randall R. Carlson; Jay S. Stout; Dwane E. Wylie, all of Lincoln; Fred W. Wagner, Walton, all of Nebr.; Malcolm Riddell, Vero Beach, Fla.

[73] Assignee: BioNebraska, Inc., Lincoln, Nebr.

[21] Appl. No.: 96,671

[22] Filed: Jun. 22, 1993

[51] Int. Cl.$^6$ ................................................. G01N 33/53
[52] U.S. Cl. .................. 435/7.92; 435/7.1; 435/7.4; 435/7.94; 436/73; 436/74; 436/76; 436/77; 436/79; 436/80; 436/81; 436/83
[58] Field of Search ............................ 435/7.1, 26, 7.4, 435/7.92, 7.94; 436/73, 74, 76, 77, 79, 80, 81, 83, 84; 530/388.26

[56] References Cited

U.S. PATENT DOCUMENTS

| | | | |
|---|---|---|---|
| 4,722,892 | 2/1988 | Meares et al. | 436/548 |
| 4,769,320 | 9/1988 | Furie et al. | 436/548 |
| 5,011,912 | 4/1991 | Hopp et al. | 436/548 |
| 5,112,606 | 5/1992 | Shiosaka et al. | 530/389.2 |
| 5,354,652 | 10/1994 | Silbergeld | 435/4 |

FOREIGN PATENT DOCUMENTS

| | | |
|---|---|---|
| 0235457A2 | 9/1987 | European Pat. Off. |
| 0286039A | 10/1988 | European Pat. Off. |
| 0369566 | 5/1990 | European Pat. Off. |
| 0369567 | 5/1990 | European Pat. Off. |
| 0446730 | 9/1991 | European Pat. Off. |
| WO90/07524 | 7/1990 | WIPO |
| 9010709A | 9/1990 | WIPO |
| WO92/01939 | 2/1992 | WIPO |
| WO92/08803 | 5/1992 | WIPO |
| WO92/13965 | 8/1992 | WIPO |
| 9216838A | 10/1992 | WIPO |
| WO92/16838 | 10/1992 | WIPO |
| 9301310A | 1/1993 | WIPO |
| 92/05658 | 1/1993 | WIPO |

OTHER PUBLICATIONS

Baker et al., *J. Biol. Chem.*, 253, 8444–8451 (1978).
Bishop et al., *PNAS–USA 83*, 5568–5572 (1986).
Chisholm et al., *Clin. Chem.*, 31, 601–605 (1985).
Clarke et al., *J. Immunol. Methods*, 137,65–72 (1991).
Fukano et al., *Biological Abstracts*, 87, Abs. No. 10613 (1989).
Iverson et al., *Science*, 243, 1184–1188 (1989).
Klein, *Immunology: The Science of Self–Nonself Discrimination*, 348 (1982).
Lewis, et al., *J. Lab. Clin. Med.*, 88, 375–388 (1976).
Lindgarde et al., *Scand. J. Immunol.*, 3, 277–285 (1974).
Merlini et al., *Clin. Exp. Immunol.*, 69, 148–156 (1987).
Reardan, *Dialog Information Services*, File 35: Dissertation Abstracts Online 1861 Jun. 90, Dialog accession No. 894111, vol. 46/07–B of Dissertaion Abstracts International, p. 2326, (1985).
Reardan et al., *Nature*, 316, 265–267 (1985).
Schuster et al., *Biologie Prospective, C.R. Colloq. 8th*, 371–376 (1993).
Shirakawa et al., *Clin. Exp. Allergy*, 22, 213–218 (1992).
Wade et al., *J. Am. Chem. Soc.*, 115, 4449–4456 (1993).
Waters et al., *DOE Methods for Evaluating Environmental and Waste Management Samples*, (1993).
Waters et al., *Govt. Reports Announcements & Index*, Issue 24 (1993).
Wylie et al., *Anal. Biochem.*, 194, 381–387 (1991).
Wylie et al., *PNAS–USA*, 89, 4104–4108 (1992).
Advertisement for BiMelyze® Mercury Assay Kit published in the Mar./Apr. 1991 issue of Journal of Analytical Toxicology (vol. 15).
Advertisement for BiMelyze® Mercury Assay Kit published in the Sep. 1991 issue of Journal of the American Water Works Association (vol. 15).
Alessio et al., "Behavior of Indicators of Exposure and Effect After Cessation of Occupational Exposure to Lead", *British J. Ind. Med.*, 38: 262–267 (1981).
Astrin et al., "δ–Aminolevulinic Acid Dehydratase Isozymes and Lead Toxicity", *Ann Ny Acad. Sci.*, 514, 23 (1987).
Baltrop et al., "Lead Binding to Human Haemoglobin", *Experientia*, 28, 76 (1972).
Bernard et al., "Metal–Induced Alterations of δ–Aminolevulinic Acid Dehydratase", *Ann. NY Acad Sci.*, 51, 41–47 (1987).
Dresel et al., "Studies on the Biosynthesis of Blood Pigments", *Biochem. J.*, 63:72 (1956).
Erikson, "The Extraction of the Urinary Coproporphyrin Chromogen and the Conversion of the Chromogen to Porphyrin", *Scand J. Clinc. Lab. Investigations*, 4, 55–62 (1952).
Friguet et al., "Measurements of the True Affinity Constant in Solution of Antigen–Antibody Complexes by Enzyme–Linked Immunosorbent Assay", *J. Immunol. Methods*, 77, 305 (1985).
Fuhr et al., "Nuclear Magnetic Resonance Studies of the Solution Chemistry of Metal Complexes. IX. The Binding of (List continued on next page.)

*Primary Examiner*—Toni R. Scheiner
*Attorney, Agent, or Firm*—Merchant & Gould, Smith, Edell, Welter & Schmidt

[57] ABSTRACT

The invention provides method and kits for detecting a metallic cation in a sample of a body fluid. The preferred method and kits include the use of at least two different types of antibodies having different specificities. In the preferred method, the sample of body fluid can be contacted with an effective amount of a capture antibody specific for a naturally occurring polypeptide that can bind the metallic cation to form a first antigen-antibody complex. An effective amount of an antibody specific for an epitope on a metallic cation-naturally occurring polypeptide complex or an antibody specific for a metallic cation is added to the first antigen-antibody complex to form a second antigen-antibody complex. The amount of the metallic cation in the sample of body fluid is determined by detecting the amount of the second antigen-antibody complex.

18 Claims, 5 Drawing Sheets

OTHER PUBLICATIONS

Cadmium, Zinc, Lead, and Mercury by Glutathione", *J. Am. Chem. Soc., 95,* 6944 (1973).

Fujita et al., "Evidence of Increased Synthesis of δ-Aminoleuvulinic Acid Dehydratase in Experimental Lead-Poisoned Rats", *Biochem. Biophys. Acta, 678,* 39–50 (1981).

Goldberg et al., "Studies on the Biosynthesis of Heme in Vitro by Avian Erythrocytes", *Blood, 11,* 821 (1956).

Gercken et al., "Determination of Lead and Other Trace Element Species in Blood by Size Exclusion Chromatography and Inductively Coupled Plasma/Mass Spectrometry", *Anal. Chem., 63:* 283–287 (1991).

Hernberg et al., "Enzyme Inhibition by Lead Under Normal Urban Conditions", *Lancet, 1,* 63–66 (1970).

Jaffe et al., "Reevaluation of a Sensitive Indicator of Early Lead Exposure", *Biol. Trace Element Res., 28,* 223–232 (1991).

Karin, "Metallothionenins: Proteins in Search of Function", *Cell, 41,* 9 (1985).

Mauzerall et al., "the Occurrence and Determination of δ-Aminolevulinic Acid and Porphobilinogen in Urine" *J. Biol. Chem., 219,* 435 (1956).

Schlick et al., "The Action of Small Doses of Lead on Erthrocyte D-Aminolevulinic Acid Dehydratase in the Mouse", *Arch. Toxicol., 43,* 213 (1980).

Tsukomoto et al., "The Role of Zinc with Special Reference to the Essential Thiol Groups in δ-Aminolevulinic Acid Dehydratase of Bovine Liver", *Biochem. Biophys. ACTA, 570,* 167–178 (1979).

Church et al., *J. Biol. Chem.,* 263:6259 (1988).

Church et al., *J. Biol. Chem., 264:* 7882 (1989).

Church et al., *Blood, 74:*2418 (1989).

Nakamura et al., *Biochim. Biophys. Acta, 925:*85 (1987).

Ohlin et al., *J. Biol. Chem., 262:13798 (1987).*

Ohlin et al., *J. Biol. Chem., 263:*7411 (1988).

Orthner et al., *J. Biol. Chem., 264:*18781 (1989).

Stearns et al., *J. Biol. Chem., 263:*826 (1988).

Wakabayashi et al., *J. Biol. Chem., 261:*11097 (1986).

Borowski et al., *J. Biol. Chem., 261:*14969 (1986).

Furie et al., *J. Biol. Chem., 253:*8980 (1978).

Furie et al., *J. Biol. Chem., 254:*9766 (1979).

Lewis et al., *Biochemistry, 22:*948 (1983).

Madar et al., *J. Biol. Chem., 257:*1836 (1982).

Malhotra, *Biochem. Cell Biol., 68:*705 (1990).

Owens et al., *J. Biol. Chem., 259:* 13800 (1984).

Pollock et al., *J. Biol. Chem., 263:*14216 (1988).

Stenflo, *J. Biol. Chem., 247:* 8167 (1972).

Tai et al., *J. Biol. Chem., 255:* 2790 (1980).

Tai et al., *J. Biol. Chem., 259:*4162 (1984).

Liebman et al., *J. Biol. Chem., 262:* 7605 (1987).

Smith et al., *Am. J. Clin. Pathol., 87:* 370 (1987).

Tharakan et al., *Vox Sang, 58:*21 (1990).

Velander et al., *Biotechnology Progress, 5:*119 (1989).

Ware et al., *J. Biol. Chem., 264:*11401 (1989).

Arquilla et al., *Biochem. J., 175:*289 (1978).

Dardenne et al., *PNAS USA, 82:*7035 (1985).

Higashiyama et al., *Biochemistry, 26:*7450 (1987).

Mesna et al., *Comp. Biochem. Physiol., 99:*181 (1991).

Pfyffer et al., *J. Neurochem.,* 49:442 (1987).

Schwabacher et al., *J. Am. Chem. Soc.,* 111:2344 (1989).

Shirakawa et al., *Chest,* 95:29 (1989).

Shirakawa et al., *Clinical Allergy,* 18:451 (1988).

Van Houdt et al., *Immunology Letters,* 32:21 (1992).

Ward et al., *Molecular Immunology,* 29:83 (1992).

Sakai, T., et al., *Clin. Chem.,* vol. 26, No. 5, pp. 625–628 (1980).

MONOCLONAL ANTIBODY ASSAY AND KIT FOR DETECTING METAL CATIONS IN BODY FLUIDS

BACKGROUND OF THE INVENTION

The burdens that exposure to lead and other metal cations places on society and individuals are massive when one considers the amount of money required for health care for those who develop metal cation-induced mental and physical disabilities, and the loss of the productive contributions that these individuals might otherwise make. For example, lead exposure can cause acute or chronic manifestations depending on the amount of lead to which a person has been exposed, and the duration of exposure. Acute exposure to lead most often leads to intestinal colic, while chronic exposure can result in various neurological symptoms, ranging from encephalopathy to psychological deficits, such as decreased intelligence and behavioral disturbances. Other metallic cations, such as mercury and cadmium, can also have adverse effects on nervous, reproductive and immunological systems.

One of the real tragedies in this situation is that, for the most part, this situation is preventable. If convenient, inexpensive, and reliable screening methods existed, they could be applied to identifying individuals at risk and to localizing environmental sources of lead and other metal cations before irreversible health effects occurs.

Most of the methods, such as atomic absorption spectrometry and anodic stripping voltametry, have been directed toward detection of metal cations, including lead, in blood. However, these procedures utilize expensive, specialized equipment that requires highly trained personnel for proper operation, thus making their use in widespread screening programs difficult, if not impossible.

As an alternative, other parameters which might serve as reliable indicators of blood metal cation contamination have been sought. Those which have been identified for lead include an increase in erythrocyte protoporphyrin (S. Piomelle, *Low Level Lead Exposure*, H. Needleman, editor, Raven Russ, NY, pp. 67–74 (1980)), a decrease in δ-aminolevulinic acid dehydratase (ALAD) enzyme activity (S. Hernberg et al., *Lancet*, I:63–66 (1970)), and a decrease in heme synthetase activity (O. Wada et al., *Ind. Health*, 10:84–92 (1972)). Of these, only the increase in erythrocyte protoporphyrin (EP) has been exploited for use as a screening method to detect the presence of lead in blood. The major difficulty with this system is that measurement of EP is not sensitive enough for accurate correlation with a blood lead concentration below 25 µg/dl, which is 2.5 times above the limit recently defined by CDC as the "safe" level of lead in blood. (L. Alessio et al., *British J. Ind. Med.*, 38:262–267 (1981).)

ALAD is a zinc-containing enzyme, and inhibition of its enzymatic activity is thought to result from displacement of zinc by metal cations including lead. (E. Jaffe et al., *Biol. Trace Element Res.*, 28:223–232 (1991).) It is generally felt that a decrease in ALAD activity is the first measurable effect of lead contamination and is the most sensitive measure of lead toxicity (Hernberg et al., cited supra.). A decrease in ALAD has been implicated in the pathogenesis of lead poisoning and, thus, may also serve as a reliable indicator of clinical status of a patient exposed to lead or other heavy metals. Astrin et al., *Ann Ny Acad. Sci.*, 514:23 (1987). The difficultly with using this parameter for development of a practical assay for blood lead is that enzyme assays are not generally convenient and rapid enough to use for a widespread screening program.

Thus, there is a need for a reliable and rapid screening and/or diagnostic assay for the presence of lead or other metallic cations in animals and the environment. In addition there is a need for an immunoassay for the quantitative detection of lead and lead-ALAD in blood. There is also a need for a rapid screening assay in a kit to determine metal cation concentrations in fluids derived from humans, animals or the environment.

SUMMARY OF THE INVENTION

The invention provides methods and kits for detecting a metallic cation in a sample of a body fluid of an animal. The preferred methods and kits can involve the use of at least two antibodies having different specificities. These antibodies fall into two general types with the second including several subtypes. In a first alternative, the method of the invention can be conducted by contacting the sample of body fluid with an effective amount of a first type of antibody, which is specific for a naturally occurring polypeptide that can bind the metallic cation to form a first antigen-antibody complex. The first antibody in this step is functioning as the capture antibody. A second type of antibody is added in an effective amount to the first antigen-antibody complex to form a second antigen-antibody complex. The second antibody is (1) specific for an epitope on a metallic cation-naturally occurring polypeptide complex and not substantially cross-reactive with the naturally occurring polypeptide alone, or (2) specific for a metallic cation or (3) specific for a combination of a complexed metallic cation and its coordination site in a metallic cation-naturally occurring polypeptide complex. The metallic cation in the sample of the body fluid is detected by determining the amount of the second antigen-antibody complex.

This first alternative of the method of the invention can also be modified by use of the first and second types of antibodies in reverse order. In this modification the second antibody functions as the capture antibody to capture the metallic cation-naturally occurring polypeptide complex.

In a second alternative, the method of the invention can be conducted by contacting a sample of the body fluid with one of the sub-types of the above-described second type of antibody to form a first antigen-antibody complex. The second antibody in this step functions as the capture antibody. The same or another subtype of the second type of antibody is then added to the first antigen-antibody complex to form a second antigen-antibody complex. If the same subtype is used, the complex will contain multiple epitopes of the same structure to enable multiple antibody binding. If the complex does not contain such epitopes, different subtypes of second type of antibody will be used. The metallic cation in the sample of body fluid is detected by determining the amount of the second antigen-antibody complex.

Assays for detecting a metallic cation in a body fluid can also involve the use of a single type of antibody. The single type of antibody has specificity for an epitope on a naturally occurring polypeptide that binds at least two metallic cations. In this version of the assay, a sample of body fluid is contacted with an effective amount of a first antibody specific for (1) an epitope or (2) a combination of a complexed metal cation and its complexation site on a metallic cation/naturally occurring polypeptide complex that binds at least two metallic cations to form a first antigen-antibody complex. An effective amount of a second antibody, which is of the same type as the first antibody but is not necessarily the same thing, is added to form a second antigen-antibody complex. The metallic cation in the sample is detected by determining the amount of the second antigen-antibody complex. The first and second antibodies can be specific for the same or different epitopes.

In a further version, a method for detecting a metallic cation in a sample of body fluid combines an antibody binding assay with an enzyme assay. In that method, a sample of body fluid containing the metallic cation is contacted with an effective amount of an antibody specific for an epitope on a metallic cation/enzyme complex or an epitope on a naturally occurring polypeptide to form an antigen-antibody complex. The metallic cation is then removed from the antigen-antibody complex, preferably by stripping with a chelator or by substitution with a different metallic cation. The enzyme activity is restored upon removal of the metallic cation and, preferably, by replacement of the metallic cations with a different metallic cation, such as the enzyme's natural cofactor. The metallic cation in the sample is detected by assaying the restored enzyme activity.

Another method of the invention provides for a determination of whether the animal has been acutely or chronically exposed to the metallic cation. The steps of the method include detecting the amount of the metallic cation bound to a first naturally occurring polypeptide, detecting the amount of the metallic cation bound to one or more, preferably two or three, other naturally occurring polypeptides, and comparing the amount of the antibody bound to the first polypeptide to that of the other polypeptides to determine if the exposure is acute or chronic. The preferred detection method is that described in the Detailed Description of the Invention.

An antibody (the first type of antibody) specific for a naturally occurring polypeptide that binds the metallic cation can serve to capture the naturally occurring polypeptide from the sample of body fluid or, in an alternate version can also serve as a detection antibody when the capture antibody is the second type of antibody. The antibody preferably is a monoclonal antibody and recognizes and binds to the naturally occurring polypeptide whether or not it is complexed with one or more metallic cations. The monoclonal antibody also preferably binds to the naturally occurring polypeptide in the body fluid in less than about 10 minutes, and with a disassociation constant of about $10^{-4}$ to $10^{-13}$. The most preferred antibody is a monoclonal antibody specific for ALAD.

An antibody (the second type of antibody) (1) specific for an epitope on a metallic cation-naturally occurring polypeptide complex, or (2) specific for a metallic cation or (3) specific for a combination of a complexed metallic cation and its coordination site in a metallic cation-naturally occurring polypeptide complex functions to allow detection of the amount of metallic cation present in the sample of body fluid or, in an alternate version, can also serve as a capture antibody. An antibody can be specific for the metallic cation portion or the naturally occurring polypeptide portion or the combination of the metallic cation and polypeptide metal complexation site of the metallic cation-naturally occurring polypeptide complex. When the antibody is specific for the naturally occurring polypeptide portion, it does not substantially cross-react with the epitopes on the naturally occurring polypeptide not complexed with the metallic cation (i.e., alone). When the antibody is specific for the metallic cation, it binds the metallic cation whether or not complexed with a naturally occurring polypeptide. When the antibody is specific for the combination, it only binds with the complex at the metal coordination site. The preferred antibody is a monoclonal antibody specific for a metallic cation. The especially preferred antibody is a monoclonal antibody specific for a toxic metallic cation, such as lead, mercury, cadmium, and gallium.

The method is preferably conducted with one of the antibodies immobilized on a substrate and the other antibody labelled with a detectable agent. Antibodies can be immobilized to a variety of solid substrates by known methods. Suitable solid substrates include materials having a membrane or coating supported by or attached to sticks, cups, flat packs, or other solid supports. Other solid substrates include cell culture plates, ELISA plates, tubes, and polymeric membranes. The preferred solid substrate is a stick coated with a polymeric membrane. The detectable agent functions to allow detection of the second antigen-antibody complex and includes fluorochromes, radioactive labels, biotin and enzymes. The preferred detectable agent is an enzyme, and the especially preferred detectable agent is horseradish peroxidase.

The amount of the second antigen-antibody complex detected is preferably proportional to the amount of metallic cation present in the sample of body fluid. The amount of the metallic cation present in a sample of body fluid can be determined by correlating the amount of the second antigen-antibody complex detected in the sample with that detected for standard amounts of the metallic cation-naturally occurring polypeptide complex. Standard solutions of the same amount of a purified naturally occurring polypeptide that binds metallic cation are mixed with different concentrations of the metallic cations ranging from 0.5 µg/dl to 50 µg/dl. The standard curve generated can be used to quantitate the amount of metallic cation in a sample. Alternatively, the standard solutions can be used to measure the disassociation constant of antibodies.

The invention also provides a preferred kit containing either two types of antibodies or one or more versions of the second type of antibody for detecting a metallic cation in a sample of body fluid. The kit preferably contains the first type of antibody and the second type of antibody. Alternatively, the kit can also contain a first antibody and a second antibody wherein both are specific for an epitope on a metallic cation/naturally occurring polypeptide that binds at least two metallic cations. A kit can also contain an antibody specific for a naturally occurring enzyme that binds the metallic cation or an antibody specific for a metallic cation enzyme complex, and substrates for measuring the enzyme activity.

One of the antibodies in the kit is preferably immobilized and the other antibody is labelled with a detectable agent. When the detectable agent is an enzyme, a means for detecting the detectable agent is supplied with the kit. The preferred means for detecting the detectable agent is an enzyme substrate that changes color upon contact with the enzyme. The kit also optionally includes standard amounts of metallic cation-naturally occurring polypeptide complexes and/or a chart with visual representations of the amount of colored product corresponding to the standard amounts of the metallic cation-naturally occurring polypeptide complexes and/or can be quantified spectrophotometrically.

The kits provide a rapid diagnostic and/or screening method for determining contamination of animals with metallic cations, especially toxic metallic cations. The kits, as disclosed herein, are especially advantageous because they provide a simple and inexpensive method to measure a large number of samples of body fluid for metal ion contamination. The kits, as disclosed herein, are also very versatile in that the kit can be designed to be quantitative or qualitative, or for use in the field or in the laboratory.

DETAILED DESCRIPTION OF THE DRAWINGS

Figure 5:
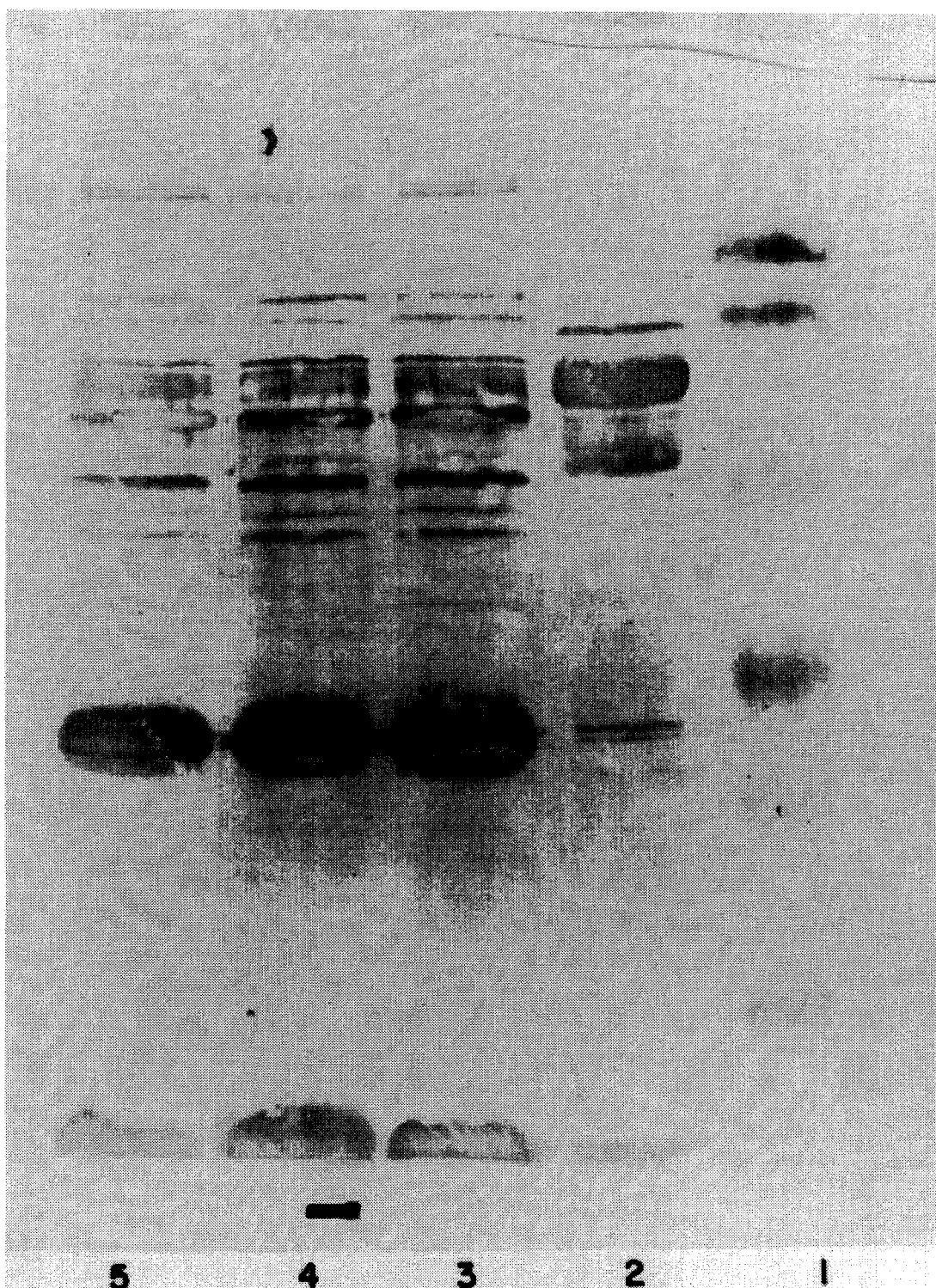

FIG. 5 shows a Western blot of metal-contaminated red cell lysates. Metal-containing proteins were detected with an antibody specific for lead cations. Hemoglobin is shown at the arrow. Lane 1 represents molecular weight standards; Lane 2: red cell lysate depleted of lead; Lane 3: red cell lysate with 55 µg/dl lead; Lane 4: red cell lysate with 20 µg/dl lead; and Lane 5: red cell lysate with 5 µg/dl lead.

DETAILED DESCRIPTION OF THE INVENTION

Methods and kits provided for in the invention allow for the detection of metallic cations in a sample of body fluid. The preferred method and kit involve the use of at least two antibodies having different specificities, i.e., a selection from the two types of antibodies. One type of antibody is specific for a naturally occurring polypeptide that binds metallic cations present in the body fluid. The other type of antibody is composed of three subtypes of differing specifications. The first subtype is specific for an epitope on a metallic cation-naturally occurring polypeptide complex. The second subtype is a specific for a metallic cation. The third subtype is a specific for a combination of a complexed metallic cation and its complexation site in a metallic cation-naturally occurring polypeptide complex. The antibody specific for metallic cation-naturally occurring polypeptide complex can be specific for either the metallic cation portion or the naturally occurring polypeptide portion of the complex. The two antibodies are combined in a preferred method that allows the detection of the metallic cation in a body fluid by determining the amount of the metallic cation bound to a naturally occurring polypeptide present in the body fluid.

A. Antibodies to Naturally Occurring Polypeptides That Can Bind the Metallic Cation Antibodies having specificity for a naturally occurring polypeptide that can bind a metallic cation are useful in method and kits of the invention. Preferably, the antibody is a mammalian IgG, IgA or IgM antibody, and more preferably the antibody is a monoclonal antibody. A monoclonal antibody specific for a naturally occurring polypeptide, preferably has a disassociation constant about $10^{-5}$ to $10^{-10}$. A disassociation constant is the ratio of the multiplication product of the concentrations of all reactants to the multiplication product of the concentrations of all products found in an equilibrium mixture, as described by the method of Friguet et al., *J. Immunol. Methods*, 77:305 (1985).

Many naturally occurring polypeptides found in animals are capable of binding one or more metallic cations. These naturally occurring polypeptides are also known as metalloproteins. A metallic cation typically serves as a cofactor essential for the activity of the naturally occurring polypeptide. The naturally occurring polypeptides can function as indicators of the presence of and the amount of the metallic cation in a body fluid, such as blood. In the case of some metallic cations, the naturally occurring polypeptide can serve to concentrate the metallic cation from the liquid portion of the blood serum. In addition, the binding of some metallic cations to the polypeptide can inactivate the function of the polypeptide. The inactive naturally occurring proteins can contribute to pathogenesis associated with exposure to metallic cations and serve as an indication of the clinical status of the animal. A naturally occurring polypeptide is one that is formed by the animal and is usually present in sufficient concentrations to be detected in the body fluid.

The naturally occurring polypeptide is capable of binding at least one, and preferably more than one different metallic cations to form a metallic cation-naturally occurring polypeptide complex. A naturally occurring polypeptide can normally contain a metallic cation cofactor that can then be displaced by binding to different metallic cation. For example, a naturally occurring polypeptide can have $Zn^{+2}$ cations as the native cofactor but also can bind to lead, mercury and cadmium cations which replace the $Zn^{+2}$ cations. Replacement of the native cofactor metallic cation with another metal cation can lead to inactivation of the function of the polypeptide. For example, replacement of $Zn^{+2}$ in ALAD by $Pb^{+2}$ results in an inactivation of ALAD enzyme activity.

Preferably, the naturally occurring polypeptide can bind an amount of the metallic cation that is proportional to the amount of metallic cation in a sample of body fluid. The naturally occurring polypeptide coordinates or binds the metallic cation with sufficient strength so that the metallic cation is retained by the polypeptide even though the polypeptide is washed with buffer solution several times. Preferably, the naturally occurring polypeptide and the metallic cation formed a coordinate covalent bond. A naturally occurring polypeptide binds or coordinates with the metallic cation preferably with an disassociation constant of about $10^{-5}$ to $10^{-10}$.

The metallic cations bound or coordinated by a naturally occurring polypeptide include cations of alkaline metals, transition metals, i.e., those elements in the periodic table with their outer most electrons in d" orbitals, the Group IIIa metal/metalloids (B, Al, Ga, In, and Tl), the Group IVa metal/metalloids (Si, Ge, S, and Pb), the Group Va metal/metalloids (As, Sb and Bi). The metallic cation can be monovalent or multivalent, but is preferably divalent and can be bound to another organic moiety, e.g., methylmercury. More preferably, the metallic cation is a toxic metallic cation known to have toxic effects on humans and other animals, as described in *Handbook on the Toxicology of Metals*, 2nd Edition, Eds: Friberg, Nordberg, Vouk, Elsevier, Amsterdam (1986). Toxic metallic cations include those that bind to sulfhydryl containing polypeptides including but not limited to lead, mercury, cadmium, copper, methylmercury, and others that do not bind sulfhydryl groups. A naturally occurring polypeptide is preferably capable of binding or coordinating with lead, mercury, methylmercury, cadmium and/or gallium cations.

Suitable examples of naturally occurring polypeptides that bind metallic cations include δ-aminolevulinic acid dehydratase (ALAD), hemoglobin (Baltrop et al., *Experientia*, 28:76 (1972)), heme synthetase (Erikson, *Scand. J. Clinc. Lab. Investigations*, 4:55–62 (1952)), coproporphyrinogen decarboxylase (Goldberg et al., *Blood*, 11:821 (1956)), ALA-synthetase (Drussel et al., *Biochem. J.*, 63:72

(1956)), human serum albumin, glutathione, pyrimidine 5' nucleotidase, protein kinase C, and metallothioneins (M. Karin, *Cell,* 41:9 (1985)). The preferred naturally occurring polypeptide that binds metallic cations is δ-aminolevulinic acid dehydratase (ALAD).

The naturally occurring polypeptide that binds metallic cations can be isolated from animal species, including humans, cows, fish, and other vertebrates. The naturally occurring polypeptide is isolated, purified, and used as an immunogen to form antibodies. Purification methods for polypeptides that bind metallic cations from body fluids are standard methods, including ammonium sulfate precipitation and chromatography, such as ion exchange, affinity and HPLC chromatography.

A naturally occurring polypeptide that binds the metallic cations is used as an immunogen to form polyclonal and monoclonal antibodies. The immunogen can contain a single polypeptide or a plurality of polypeptides such as found in a red cell lysate or serum. The immunogen can also be a naturally occurring polypeptide complexed with one or more metallic cations. Typically an animal that is a different species than that from which the naturally occurring polypeptide is isolated is immunized with the purified polypeptide. The immunogen is administered parenterally, most often, either subcutaneously or intraperitoneally in an adjuvant. Administration of the immunogen is repeated periodically and preferably for at least four injections. After repeated immunizations, polyclonal serum can be harvested from the animal.

Preparation of monoclonal antibodies is achieved by the standard technique, as described in *Antibodies: A Laboratory Manual,* Harlow & Lane; Cold Spring Harbor (1988). Briefly, spleens are harvested from animals immunized with the immunogen as described above. Spleen cells are separated and fused with the immortal myeloma cells using polyethylene glycol. The fused hybridoma cells are selected and cultured in vitro. The hybridoma cell culture fluids are tested for the presence of hybridoma antibodies having a certain specificity.

The selection technique for identifying the appropriate first type monoclonal antibody is an important aspect for determining the immunospecificity desired according to the invention. The hybridoma cells culture fluids are tested for the presence of antibodies specific for the naturally occurring polypeptide with an ELISA conducted by standard methods.

Additional screening methods can also be employed to further select the monoclonal antibody having the desired specificity. One or more of these screening methods can be employed to select a monoclonal antibody having a particular specificity. Those additional screening methods include screening for monoclonal antibodies that can also bind to the naturally occurring polypeptide when it is a part of a metallic cation-naturally occurring polypeptide complex. Another preferred monoclonal antibody recognizes and binds the naturally occurring polypeptide whether or not it is complexed with one or more metallic cations. In addition, the hybridoma cell culture fluid can also be selected for monoclonal antibodies that are specific for the biologically active form of the naturally occurring polypeptide. Alternatively and optionally, a monoclonal antibody specific for a naturally occurring polypeptide that binds the metallic cation can be screened for specificity for the naturally occurring polypeptide from several different species of animals.

The selection for a monoclonal antibody specific for biologically active forms of the naturally occurring polypeptide can be accomplished by contacting the hybridoma cell culture fluid containing monoclonal antibodies with the naturally occurring polypeptide to form an antigen-antibody complex, separating the antigen-antibody complex, and then assaying the antigen-antibody complex for functional activity. For example, if the naturally occurring polypeptide is an enzyme, the antigen-antibody complex can be assayed for enzymatic activity.

Suitable monoclonal antibodies are those specific for ALAD, hemoglobin, glutathione, human serum albumin, and the metallothioneins. The preferred monoclonal antibody is specific for ALAD. Suitable polyclonal antibodies are those to human serum. Some of these antibodies are commercially available.

In the preferred version, monoclonal antibodies to the naturally occurring polypeptide ALAD are formed. ALAD is an enzyme that is known to bind $Zn^{+2}$ cations as its native metallic cation cofactor, however, the enzyme is also known to bind or coordinate with lead, mercury, cadmium, or copper as well. Bernard & Lauwerys, *Ann. NY Acad. Sci.,* 51:41–47 (1987). Bovine ALAD is purified from erythrocyte cell lysates, as described by the method of Fujita et al., *Biochem. Biophys. Acta,* 678:39–50 (1981) using ammonium sulphate precipitation and heat treatment followed by DEAE and ultragel ACA34 chromatography. An effective amount of purified bovine liver ALAD is injected with adjuvant into mice. Polyclonal serum can be harvested from the mice at this point and the presence of ALAD-specific antibodies is monitored by ELISA. The spleen is fused to form hybridoma cell lines. Monoclonal antibodies specific for ALAD, whether or not complexed with lead, are selected. Monoclonal antibodies are further selected for specificity for the biologically active form of ALAD by assaying ALAD monoclonal antibody complexes for ALAD enzyme activity by the method of Tsukomoto et al., *Biochem. Biophys. ACTA,* 570:167–178 (1979). The preferred monoclonal antibody specific for bovine ALAD also recognizes and binds to human ALAD.

The invention also provides a method for identifying naturally occurring polypeptides that can bind metallic cations present in body fluids. The method involves using a Western blot assay with monoclonal antibodies specific for metallic cations. Samples of a body fluid from an animal are treated so that any cells in the body fluid are lysed. The sample of the body fluid is then incubated with various concentrations of a metallic cations, preferably the concentrations range from 0.5 μg/dl to 50 μg/dl of the metallic cation or can be obtained from animals dosed experimentally with varying amounts of metallic cations. The metallic cation-treated sample is then subjected to electrophoresis. The proteins separated by electrophoresis are transferred to a nitrocellulose membrane. The separated proteins on the nitrocellulose membrane are then incubated with monoclonal antibodies labelled with a detectable agent and specific for the metallic cation added to the initial solution. Separated proteins binding to the monoclonal antibodies specific for the metallic cation are identified by detecting the detectable agent. The polypeptides that have bound the metallic cation are identified by molecular weight and can be eluted from an electrophoresis gel run in parallel. The polypeptides that bind metallic cations can be identified by comparison to a panel of known polypeptides that bind metallic cations to help identify the polypeptide. Comparison methods can include Western blots, PAGE, HPLC, other chromatography. Any new polypeptides identified as binding to metallic cations can be further characterized by standard methods for amino acid analysis and enzyme activity.

The method allows the identification and characterization of naturally occurring polypeptides that can bind metallic cations and also allows the identification of naturally occurring polypeptides that can bind metallic cations present at very low concentrations.

B. Antibodies that Can Detect the Presence of the Metallic Cation

Antibodies of the second type are useful in the methods and kits of the invention. The antibodies are preferably mammalian antibodies of the IgG, IgA and IgM class, and more preferably are monoclonal antibodies. One version of this type of antibody is specific for an epitope either as the metallic cation portion or as the naturally occurring polypeptide portion of the metallic cation-naturally occurring polypeptide complex. An epitope on the metallic cation-naturally occurring polypeptide complex can be (1) the metallic cation or (2) peptide epitope or (3) the metallic cation-peptide coordinate epitope recognized only when the naturally occurring polypeptide is complexed with the metallic cation. The antibody can also be specific for a metallic cation whether or not bound to a naturally occurring polypeptide. The preferred monoclonal antibodies are specific for a metallic cation and also, more preferably, bind to and recognize the metallic cation portion of a metallic cation-naturally occurring polypeptide complex. The monoclonal antibodies are specific for an epitope only found on a metallic cation-naturally occurring polypeptide complex, i.e., the monoclonal antibody does not substantially cross-react with the naturally occurring polypeptide not complexed with the metallic cation (i.e., alone).

Monoclonal antibodies specific for metallic cations or for a metallic cation-naturally occurring polypeptide complex also preferably do not substantially cross-react with other metallic cations or other metallic cation-naturally occurring polypeptide complexes. A monoclonal antibody is substantially non-crossreactive with other antigens if it does not significantly react with the antigen over background levels in a standard ELISA reaction. Preferably, a non-crossreactive antigen binds to the antibody with a disassociation constant of $10^{-4}$ or less. Monoclonal antibodies of the invention preferably have a disassociation constant of about $10^{-4}$ to $10^{-13}$, and preferably about $10^{-7}$ to $10^{-11}$. The monoclonal antibody specific for a metallic cation or a metallic cation-naturally occurring polypeptide complex can be used to detect the amount of a metallic cation present in a sample of a body fluid or can be used as capture antibody to remove metallic cation containing naturally occurring polypeptides from the sample of body fluid. The preferred monoclonal antibodies are capable of detecting metallic cations in a sample of body fluid with as low as 1 µg/dl (10 ppb) of metallic cation.

Metallic cations include cations of the alkali earth metals, the transition metals, i.e., those elements in the periodic table with their outermost electrons in the d" orbitals, Group IIIa metal/metalloids (B, Al, Ga, In, and Tl), Group IVa metal/metalloids (Si, Ge, S, and Pb), and Group Va metal/metalloids (As, Sb and Bi). The metallic cation can be monovalent or multivalent, but are preferably divalent and can be bound to another organic moiety, e.g. methylmercury. More preferably, the metallic cation is a toxic metallic cation known to be harmful to humans and other animals, as described in *Handbook on the Toxicology of Metals,* cited supra. Typically, toxic metallic cations are those that bind to sulfhydryl containing polypeptides including lead, mercury, cadmium, copper, and methylmercury. The preferred metallic cations are lead, mercury, cadmium, and gallium.

Suitable examples of monoclonal antibodies specific for metallic cations include monoclonal antibody 4A10 specific for mercury. This monoclonal antibody has a disassociation constant of $2.3 \times 10^{-9}$M for $HgCl_2$. This monoclonal antibody does not substantially cross-react with barium chloride, cadmium chloride, chromic chloride, copper chloride, ferrous sulfate, gold chloride, nickel chloride, selenium oxide, silver chloride, and zinc chloride. Monoclonal antibodies to lead have also been generated. The preferred monoclonal antibody is specific for Pb and does not crossreact with other similarly structured metal ions.

Monoclonal antibodies specific for lead and mercury cations have been deposited with the American Type Culture Collection (ATCC) on Mar. 13, 1990. Monoclonal antibody BN No. 4A10B4, ATCC Accession No. HB 10381, has a dissociation constant for mercury cation of less than about $10^{-9}$ but does not bind cadmium, copper, zinc, lead, nickel and cobalt cations to any appreciable extend.

Antibodies of the invention can also bind to an epitope of a metal cation naturally occurring polypeptide complex such as Pb complexed with ALAD. Preferably, the antibody does not substantially crossreact with other metallic cation naturally occurring polypeptide complexes such as Zn complexed with ALAD. Optionally, the antibody may also be capable of binding to the uncomplexed metallic cation. This antibody is also substantially non-crossreactive with the naturally occurring polypeptide uncomplexed with the metallic cation such as ALAD without Pb. The naturally occurring polypeptide complexed with the metal cation can also be an enzyme so that the antibodies can recognize a metal cation enzyme complex. A preferred monoclonal antibody is a monoclonal antibody specific for lead complexed with ALAD. An antibody with specificity for lead-ALAD and designated 14F11 has been deposited with the American Type Culture Collection, Rockville, Md. on Apr. 16, 1993 and given Accession No. HB 11330.

A metallic cation-naturally occurring polypeptide complex can be formed by incubating a naturally occurring polypeptide that binds the metallic cation with the metallic cation or can be formed by exposure of the animal to the metallic cation in vivo. A naturally occurring polypeptide that is known to bind metallic cations can be isolated and purified from an animal or a naturally occurring polypeptide that binds metallic cations can be identified by a method of the invention. A naturally occurring polypeptide can have a native metallic cation cofactor and can bind to a different metallic cation which then displaces the native metallic cation cofactor. A naturally occurring polypeptide binds to the metallic cation with sufficient strength to withstand several washings of the complex. Preferably, a naturally occurring polypeptide binds to or coordinates with the metallic cation with a disassociation constant of $10^{-4}$ to $10^{-13}$.

Suitable examples of naturally occurring polypeptides that bind to metallic cations include δ-aminolevulinic dehydratase (ALAD), hemoglobin, heme synthetase, coproporphyrinigen decarboxylase, ALA synthetase, human serum albumin, glutathione, pyrimidine 5' nucleotidase, protein kinase C, and metallothioneins. The preferred metallic cation-naturally occurring polypeptide complex is lead-ALAD.

The strategy for forming monoclonal antibodies immunoreactive with bare or uncomplexed metallic cations is that described in copending application U.S. Ser. No. 324,392 filed on Mar. 14, 1989. The monoclonal antibodies to metallic cations are formed in response to an immunogen having characteristics that allow for the metallic cation to remain in a substantially exposed state so that it is available to react with the cells of the immune system.

The immunogen compounds for generation of the specific immunogenicity of the monoclonal antibodies for metallic cations are based upon the hapten-carrier concept. In the present invention, hapten is coordinated at the end of a spacer arm covalently bonded to a carrier. The spacer arm is adapted so as to be semi-rigid and to hold the metallic cation in an exposed position relative to the carrier. This arrangement is also adapted to maintain the metallic cation in a substantially exposed state. These factors combine substantially to avoid chelating, uncovering or inclusion of the metallic cation by the spacer and/or the carrier.

The spacer arm, as characterized above, may be an oligopeptide, an aliphatic compound, or an aliphatic fragment. In the later two instances, the aliphatic compound or fragment may be covalently bonded to the carrier by means of a Schiff base reaction with an aldehyde group; an amide reaction with an amine or carboxylic acid group using a peptide activator such as carbodiimide, acid chloride and the like; and an ester reaction with a hydroxyl or carboxylic acid group using a Shotten-Bauman reaction or azide or acid catalysis reaction; a sulfide reaction using sulfide coupling agent or other known coupling reactions for joining organic molecules to proteins. See, for example, E. A. Kabat, *Structural Concepts in Immunology and Immunochemistry*, 2nd edition, Holt, Rheiner & Winston, New York (1976) (a review text of such methods); and Jaime Eyzaguirre, *Chemical Modification of Enzymes: Active Site Studies*, Chichester, Westsussex, England, Halsted Press (1987). The oligopeptide, aliphatic compound or fragment will contain backbone groups which provide semi-rigidity to the spacer arm. Preferred groups for developing this semi-rigidity include peptide bonds, olefin bonds, olefinic conjugated systems, ester groups and enone groups. Optionally, one or more aromatic rings can be incorporated into the spacer arm to stimulate the development of an immune response.

In general, the oligopeptide spacer arm has the following formula:

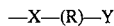

wherein X is a coupling group that will bond to the carrier, R is one or more amino acid residues, and Y is the Lewis acid or base group for metallic cation coordination.

In general, the aliphatic compound or fragment spacer arm has the following formula:

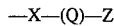

wherein X is a coupling group that will bond to the carrier, Q is a semi-rigid aliphatic moiety containing ester amide keto, olefin or aromatic groups and the like, and Z is the Lewis acid or base group for metallic cation coordination.

Preferably, an oligopeptide or aliphatic compound is used as the spacer arm for a metallic cation. In this instance, the pendant Lewis base groups will preferably be positioned at the spacer arm and remote from the carrier. These Lewis base groups function as a coordination site or sites for the metallic cation. It is preferable that the deformity of the electron shells of the Lewis base groups and the metallic cations be approximately similar. Accordingly, sulfur groups can serve as the Lewis base groups when the metal cations are transition metals or inert transition elements. Nitrogen-containing groups are preferably employed as Lewis base groups when aluminum, lithium, boron, strontium, and magnesium are the metallic cations.

Carrier molecules are typically large molecular weight proteins that can function to concentrate the carrier spacer arm metallic cation complex. Suitable carrier molecules include proteins that are not enzymatically active such as bovine serum albumin (BSA) or keyhole limpet hemocyanin (KLH). Once formed, the carrier spacer arm is incubated with the metallic cation to form an immunogen. The immunogen is administered to an animal parenterally, most often, either subcutaneously or intraperitoneally with an adjuvant. Administration of the immunogen is repeated at least four times. After repeated immunization, polyclonal sera can be harvested.

Monoclonal antibodies are formed by standard methods, as described previously. Briefly, spleens from the immunized animals are harvested and spleen cells separated. Spleen cells are fused with myeloma cells to form hybridoma cells. Hybridoma cells are selected and incubated in vitro. The presence of monoclonal antibodies specific for metallic cations in the hybridoma cell culture medium is assayed by ELISA. Hybridoma secreting monoclonal antibodies are selected for specificity to metallic cations.

The monoclonal antibodies can be selected by one or more selection techniques. One selection technique selects for the ability of the monoclonal antibodies to immunoreact with the metallic cation and to not substantially cross-react with the carrier spacer arm conjugate. The monoclonal antibodies can also be selected to not substantially cross-react with other metallic cations. A monoclonal antibody is not substantially crossreactive with an antigen if it does not react with that antigen significantly above background level in a standard ELISA assay. Preferably, the monoclonal antibody binds to a non-crossreactive antigen with a disassociation constant of $10^{-4}$ or less. The monoclonal antibodies can also be selected to bind to the metallic cation portion of a metallic cation-naturally occurring polypeptide complex. The preferred monoclonal antibody is specific for a metallic cation, does not substantially cross-react with the carrier spacer arm or other metallic cations, and binds to the metallic cation portion of a metallic cation-naturally occurring polypeptide complex.

A preferred application contemplates the production of monoclonal antibodies specific for the mercuric cation or another toxic heavy metal cation. The heavy metal cation is combined into an immunogen compound, as described above, and suspended in aqueous medium. The preferred protein carrier for the immunogen compound in this instance is keyhole limpet hemocyanin. The preferred spacer arm in this instance is an oligopeptide which has sulfhydryl groups capable of coordinating with the heavy metal cation. Glutathione is especially preferred as the spacer arm. The suspension of the immunogen compound is used to immunize a host mammal, such as a mouse, following the techniques outlined above. The laboratory strain of mouse designated BALB/c is particularly preferred.

Antibody producing cells of the immunized host spleen are collected and converted into a suspension. These spleen cells are fused with immortal cells. Preferably myeloma cells of the same animal species as the immunized host are used as a fusion partner. Typically, a cell fusion promoter, such as polyethylene glycol, is employed to cause formation of the hybridoma cells. The hybridoma cells are diluted and cultured in a medium which does not allow for the growth of unfused cells.

The monoclonal antibodies produced and secreted by the hybridomas are thereafter assayed for the ability to bind specifically with the heavy metal cations used for immunization. They are further selected for lack of cross-reactivity with the carrier and with carrier spacer arm. The preferred assay method in this context is an enzyme-linked immunosorbent assay.

The resulting monoclonal antibodies are specific for toxic heavy metal cations and exhibit strong disassociation constants for the heavy metal cations when in the presence of spacer arm, the spacer arm carrier composition, and other similarly structured cations. Preferred monoclonal antibodies are selectively immunoreactive with cations of mercury, lead, cadmium, strontium, nickel, cobalt, gold, or arsenic.

Polyclonal and monoclonal antibodies specific for a metallic cation-naturally occurring polypeptide complex can be formed by immunizing an animal with the naturally occurring polypeptide complexed with the metallic cation, as described previously. The antibodies formed and selected can be specific for the metallic cation portion of the metallic cation-naturally occurring polypeptide complex or a peptide epitope on the naturally occurring polypeptide portion of the metallic cation-naturally occurring polypeptide complex. A monoclonal antibody specific for an epitope on the naturally occurring polypeptide portion of the complex does not substantially cross-react with epitopes on the naturally occurring polypeptide not complexed with the metallic cation. The preferred monoclonal antibodies are selected for specificity for an epitope found on the metallic cation-naturally occurring polypeptide complex and not found on the naturally occurring polypeptide complexed with a different metallic cation. The monoclonal antibodies can also be further selected to not substantially cross-react with other metallic cation-naturally occurring polypeptide complexes. The especially preferred monoclonal antibody is a monoclonal antibody that is specific for lead-ALAD complex and does not substantially cross-react with ALAD.

C. Method for Detecting a Metallic Cation in a Body Fluid

The invention provides a preferred method for detecting a metallic cation in a sample of a body fluid utilizing two different antibodies. The method involves contacting an effective amount of a capture antibody of the first type with the sample of body fluid suspected of containing the metallic cation to form a first antigen-antibody complex. This step functions to capture a naturally occurring polypeptide that binds the metallic cation from the body fluid. Then, an effective amount of the second type of antibody is added to the first antigen-antibody complex to form a second antigen-antibody complex. This antibody can be any of the three specific subtypes mentioned above. The antibody can also be specific for an epitope formed in response to a metallic cation bound to a spacer arm-carrier conjugate immunogen. The second antigen-antibody complex includes the first type of antibody, the naturally occurring polypeptide, the metallic cation and the second type of antibody. The amount of the metallic cation in the sample of body fluid is determined by detecting the amount of the second antigen-antibody complex. The amount of the second antigen-antibody complex is preferably proportional to the amount of the metallic cation in the sample.

A sample of the body fluid suspected of containing a metallic cation is obtained from an animal species. All animal species can contain metallic cations, especially toxic metallic cations. Suitable body fluids include any fluid that might contain a naturally occurring polypeptide that binds the metallic cation. The preferred body fluids are those that are easily obtained from the animal, including blood, urine, saliva, and cerebral spinal fluid. Preferably the sample of body fluid is treated with a lysing agent to lyse cells present in the body fluid. Cells in the sample of body fluid can also contain a naturally occurring polypeptide that bind the metallic cation. Suitable lysing agents include surfactants such as Tween 80, Nonidet p40, Triton X-100, and the like.

The first type of antibody selectively binds to the naturally occurring polypeptide in the sample of the body fluid to isolate the naturally occurring polypeptide from other proteins and polypeptides present in the sample. The antibody will preferably bind the naturally occurring polypeptide whether or not it is complexed with one or more metallic cations. A polyclonal antiserum to red cell proteins or serum proteins can be used to effectively capture substantially all polypeptides that bind the metallic cation and provides for a sensitive detection of the metallic cation contamination of the body fluid. Preferably, the antibody is a monoclonal antibody and, more preferably, is a monoclonal antibody specific for an epitope shared by the naturally occurring polypeptide from many animal species. The especially preferred monoclonal antibody is specific for ALAD. An effective amount of the antibody is that amount of antibody that is sufficient to bind substantially all of the naturally occurring polypeptide from the sample of body fluid. An effective amount of the antibody can be determined by measuring the total protein level in the sample of body fluid by standard methods.

The second type of antibody is added to the first antigen-antibody complex and allows the determination of the amount of the metallic cation present in the sample. The antibody can be specific for the metallic cation portion or for the naturally occurring polypeptide portion or for the combination of the metallic cation and coordinate polypeptide portion of the metallic cation-naturally occurring polypeptide complex. The antibody can also be specific for a metallic cation not complexed with a naturally occurring polypeptide. When the antibody is specific for the naturally occurring polypeptide portion or the combination of the metallic cation-naturally occurring polypeptide complex, it does not substantially cross-react with the naturally occurring polypeptide not complexed with the metallic cation (i.e., alone). The preferred antibody is a monoclonal antibody for a metallic cation. The especially preferred antibody is a monoclonal antibody for a toxic metallic cation, such as lead, cadmium, mercury, and gallium. An effective amount of the antibody specific for an epitope on a metallic cation-naturally occurring polypeptide complex is that amount that is sufficient to bind substantially all of the first antigen-antibody complex.

The preferred method of the invention can also be conducted in reverse order. A sample of the body fluid containing the metallic cation bound to a naturally occurring polypeptide can first be contacted with a capture antibody that is of the second type to form a first antigen-antibody complex. For example, monoclonal antibodies specific for lead can be used to bind lead and lead complexed with the naturally occurring polypeptides in the sample of the body fluid. An antibody of the first type can then be added to form the second antigen-antibody complex. The amount of the metallic cation in the sample of body fluid is determined by detecting the amount of second antigen-antibody complex. The amount of the second antigen-antibody complex is preferably proportional to the amount of metallic cation present in the sample of body fluid.

The preferred method of the invention can also be practiced through use of the second type of antibody as both the capture and detection antibody. If multiple epitopes of the same structure appear on the metallic cation-naturally occurring polypeptide complex, the same subtype of second antibody can be used twice. If not, then differing subtypes will be used. Capture and detection procedures are conducted as described for the foregoing versions of the method of the invention.

The antibody used first to contact the sample of the body fluid is preferably immobilized onto a solid substrate. The antibody can be immobilized onto a solid substrate by a variety of methods, as described in *Antibodies: A Laboratory Manual*, cited supra.

Suitable solid substrates include materials having a membrane or coating supported by or attached to sticks, synthetic glass, agarose beads, cups, flat packs, or other solid supports. Other solid substrates include cell culture plates, ELISA plates, tubes, and polymeric membranes. The preferred solid substrate is a stick coated with a polymeric membrane.

An antibody that is added to the first antigen-antibody complex to form a second antigen-antibody complex is preferably labelled with a detectable agent so that the second antigen-antibody complex can be easily detected. The antibody can be labelled with a detectable agent by standard methods, as described in *Antibodies: A Laboratory Manual*, at pages 319–358, cited supra. The method for labelling the antibody with a detectable agent depends on the type of detectable agent and is conducted so that the labelling of the antibody does not interfere with the capability of the antibody to bind to the antigen.

Suitable detectable agents include enzymes, radioactive labels, fluorochromes, and biotin. The preferred detectable agents are enzymes, such as horseradish peroxidase, alkaline phosphatase, and β-galactosidase.

The means for detecting the second antigen-antibody complex depend on the detectable agent coupled to the antibody. If the detectable agent is a radioactive label, like $I^{125}$ or $S^{35}$, then the second antigen-antibody complex is detected by measuring radioactive decay in a scintillation counter. If the detectable agent is a fluorochrome, the second antigen-antibody complex is detected by measuring fluorescent energy emissions spectrophotometrically. If the detectable agent is an enzyme, the second antigen-antibody complex is detected by enzymatic conversion of a substrate.

In a preferred version, the detectable agent is an enzyme and the means for detecting the detectable agent is a substrate for that enzyme. The substrate is preferably a compound that changes color as a result of the enzymatic activity. A sufficient amount of the substrate is added to ensure that the amount of substrate converted is proportional to the amount of the second antigen-antibody complex present in the sample.

The metallic cation present in the sample of body fluid can be detected by determining the amount of the second antigen-antibody complex and comparing it to a standard curve that correlates the amount of the second antigen-antibody complex with a known concentration of the metallic cation. The immunoassay, as described above, can be run with standard amounts of the naturally occurring polypeptide purified and mixed with different concentrations of the metallic cation ranging from about less than 0.5 µg/dl to 50 µg/dl. For example, standard solutions containing the same amount of purified ALAD can be mixed with different concentrations of lead cations ranging from about 0.5 µg/dl up to 50 µg/dl. These standard solutions are then contacted with an antibody specific for ALAD to form a first antigen-antibody complex. An antibody specific for the lead labelled with horseradish peroxidase is then added to the first antigen-antibody complex to form the second antigen-antibody complex. The amount of the second antigen-antibody complex is measured by conversion of the substrate for horseradish peroxidase, 2,2'-azino-di-[3-ethyl-benzothiazoline sulfonate(6)] (ABTS). ABTS is converted to a colored product which is measured spectrophotometrically at 405 nanometers. A standard curve is constructed by plotting the amount of lead cation added to the original sample against the amount of substrate converted.

In a preferred version, the method detects the amount of lead cations present in human blood. A blood sample is obtained and treated with Triton X-100 to lyse the red blood cells. The sample is then contacted with an antibody specific for ALAD immobilized on an ELISA plate to form a first antigen-antibody complex. The plate is then washed to remove uncomplexed proteins, and an antibody specific for lead and labelled with horseradish peroxidase is added to the first antigen-antibody complex. After incubation and washing, the substrate for horseradish peroxidase, ABTS is added. Conversion of the substrate to the product is measured spectrophotometrically at 405 nanometers. The amount of lead cation in the blood sample is determined by reference to the standard curve.

This method can be used to detect a plurality of different metallic cation-naturally occurring polypeptide complexes in a body fluid. For example, immunoassays can be run concurrently using several different antibodies specific for different naturally occurring polypeptides that bind to metallic cations. For example, the immunoassay can be run with either an antibody specific for ALAD, glutathione, and/or metallothionein. The amount of the metallic cation, such as lead, complexed with each of these polypeptides in the blood sample can be compared and can be used to determine the amount and duration of the metallic cation exposure.

A method of the invention can also provide for a determination of whether an animal has been exposed acutely or chronically to the metallic cation. While not in any way meant to limit the invention, it is believed that some naturally occurring polypeptides, such as ALAD, bind to the metallic cation within a short time of exposure (e.g. 3 hours or less) and other naturally occurring proteins do not bind the metallic cation until there has been a prolonged exposure (e.g. at least 24 hours). A comparison of the amount of the metallic cations bound by these two different types of polypeptides can indicate whether the exposure is acute or chronic. A comparison of metallic cation binding by the acute binding protein and two or more of the chronic binding protein can indicate whether there has been recent acute exposure as well as chronic exposure. For example, if substantially all of the metallic cation is detected bound to a polypeptide that binds the metallic cation within a short time of exposure, such as ALAD, it is likely that the animal was acutely exposed. Binding of substantially all of the metallic cation means preferably binding of about 80–100% of the total metallic cation detected binding to both types polypeptides and more preferably about 90–100%.

If the metallic cation is detected bound to several naturally occurring polypeptides, including those polypeptides that bind the metallic cation after a short and a long exposure, then it is likely the animal has been chronically exposed to the metallic cation. For a chronic exposure, preferably binding to the first type of naturally occurring polypeptide is about 10–60%, and binding to the second type of naturally occurring polypeptide is about 20–70% of the total metallic cation bound to both polypeptides.

The steps of the method include detecting the amount of the metallic cation bound to a first type of naturally occurring polypeptide, detecting the amount of the metallic cation bound to one or more second type of naturally occurring polypeptides and comparing the amount of metallic cation bound by the first type of polypeptide to the other polypeptides. Preferably the first type of polypeptide is a naturally occurring polypeptide that binds the metallic cation within a short period of time after exposure, preferably within about 3–24 hours. The preferred polypeptide that binds the metallic cation after a short period of exposure is ALAD. The second type of polypeptide is preferably a polypeptide that binds the metallic cation after a longer duration, preferably after at least about 24 hours, and more preferably about 24–72 hours. The preferred polypeptide that binds the metallic cation after a longer exposure is hemoglobin.

The amount of metallic cation bound by a naturally occurring polypeptide upon an acute exposure (i.e., the first type) can be compared to the amount of metallic cation bound by one or more naturally occurring polypeptides that bind to metallic cations after a chronic exposure (i.e., second type). In a preferred version, the amount of metallic cation bound to a first type of polypeptide, such as ALAD, is compared to the amount of metallic cation bound to a second type of polypeptide, such as hemoglobin.

The amount of metallic cation bound to the polypeptides can be detected by the immunoassay method of the invention. For example, the amount of a metallic cation such as lead bound to a first type of naturally occurring polypeptide can be determined by an immunoassay employing an antibody specific for ALAD as capture antibody and an antibody specific for lead cation to detect the amount of ALAD lead complex. The amount of lead bound to ALAD can be detected by comparison to a standard curve prepared using known standard as described previously. The amount of metallic cation such as lead bound to one or more other naturally occurring polypeptides, such as hemoglobin, can be determined in a similar manner except that the capture antibody in this case is an anti-hemoglobin antibody. The amount of the metallic cation bound preferably is measured as a percentage of the total amount of metallic cation detected binding to each of the polypeptides.

The immunoassay method of the invention can be optionally performed in a number of different variations depending on the specificity of the antibody employed. Some of these alternate embodiments are described below.

Not all embodiments of the method of the invention require two antibodies having different specificities. For example, a method of the invention includes using a single antibody specific for a naturally occurring polypeptide or metallic cation-naturally occurring polypeptide complex to serve as a capture antibody. The capture antibody binds the naturally occurring proteins that bind the metallic cation from the sample of body fluid. The naturally occurring polypeptide in this case is an enzyme whose activity is inhibited by the binding of the metallic cation. Once the naturally occurring polypeptide that binds the metallic cation is immobilized by the capture antibody, enzyme activity is measured. Enzyme activity can be restored by removal of the metallic cation that inhibits the enzyme activity. Removal of the metallic cation can be accomplished by using a chelating agent to bind the metallic cation or by adding an excess of the native cofactor or using a combination of both treatments. After removal of the metallic cation that inhibits enzyme activity, the restored enzyme activity is measured. The amount of the restored enzyme activity is an indicator of the amount of the inhibiting metallic cation bound to the enzyme.

Typically, enzymes that bind to metallic cations and assays for their activity are known to those of skill in the art. For example, ALAD is an enzyme that binds to lead cations and whose activity is inhibited by the binding of lead cations in place of the native cofactor $Zn^{+2}$. Tsukamoto et al., *Biochem. Biophys. ACTA*, 570:167 (1979). An antibody specific for ALAD or lead-ALAD can be used to capture the ALAD-Pb complexes from the body fluid. The enzyme activity of ALAD in the Pb-ALAD complexes can be determined by standard methods as described in Mauzerall and Granick, *J. Biol. Chem.*, 219:435 (1956). Removal of the lead cation can be accomplished by incubating the lead-ALAD in the presence of a chelator such as ethylene diaminetetraacetic acid followed by an excess of $Zn^{+2}$ ions. After removal of the lead cations, the restored enzyme activity can again be measured. The amount of restored enzyme activity can be used to determine the amount of lead cation bound to ALAD.

In another alternate version, a method of the invention can employ a single antibody specific for a naturally occurring polypeptide that binds at least two metallic cations per polypeptide. An antibody specific for a naturally occurring polypeptide that binds at least two metallic cations is first used as a capture antibody to immobilize the naturally occurring polypeptide from the sample of body fluid. The same antibody can then be employed to detect the amount of the naturally occurring polypeptide that binds at least two of the metallic cations immobilized. Preferably, the antibody is specific for (1) the metallic cation or (2) the metallic cation portion of, or (3) the combination of metallic cation and coordinate polypeptide portion of the metallic cation-naturally occurring polypeptide complex. For example, an antibody specific for lead cations can be used to capture a naturally occurring protein that binds at least two lead cations per polypeptide, such as ALAD. While not in any way meant to limit the invention, it is believed that the other lead cation bound to the polypeptide can then be detected. Once the naturally occurring polypeptide that binds at least two of the metallic cations per polypeptide is captured or immobilized, the amount of bound lead cation can be detected using the same antibody specific for lead cations but labelled with a detectable agent, as described previously.

These alternate embodiments of the immunoassay method of the invention can also provide for a rapid, low cost detection of metallic cation contamination in a sample of body fluid.

D. Immunoassay Kit for Determining the Amount of a Metallic Cation in a Sample of Body Fluid The invention also provides kits for detecting one or more metallic cations in a sample of body fluid. The preferred kit contains at least two antibodies having different specificities. One of the antibodies can be a first type antibody while the other antibody can be a second type antibody. Alternatively both antibodies can be of the second type as described above. One of the antibodies in the kit is preferably immobilized on a substrate and the other type of antibody is preferably labelled with a detectable agent. The antibody immobilized on the substrate is preferably not labelled with the detectable agent. The antibody not immobilized on the substrate is preferably labelled with a detectable agent.

The antibodies are present in the kit in an amount effective to bind to and detect substantially all of the naturally occurring polypeptide that binds the metallic cation in the sample of body fluid.

The preferred antibody specific for a naturally occurring polypeptide that can bind metallic cation is capable of binding substantially all of the naturally occurring polypeptide from the sample of body fluid in about 10 minutes or less. The especially preferred antibody specific for a naturally occurring polypeptide that binds the metallic cation is an antibody specific for ALAD.

The preferred antibody specific for an epitope (polypeptide portion or combination) on metallic cation-naturally occurring polypeptide complex or a metallic cation is capable of detecting concentration of the metallic cation in a sample of fluid containing at least about 1 µg/dl metallic cation. The especially preferred antibody is an antibody specific for lead cations.

The kit can contain any number of combinations of the different types and subtypes of antibodies. For example, the kit can contain an antibody specific for a metallic cation and several different antibodies specific for different naturally occurring polypeptides that can bind the metallic cation. Alternatively, the kit can contain several different antibodies specific for different metallic cations and one antibody specific for a naturally occurring polypeptide that can bind the metallic cations. Alternatively, the kit can contain a plurality of antibodies specific for metallic cations and a plurality of antibodies specific for naturally occurring polypeptides that can bind the metallic cations. The kit can also containing a third type of anti-immunoglobulin antibody that is anti-IgG, anti-IgM, or anti-IgA, preferably labelled with a detectable agent. The preferred kit contains one monoclonal antibody specific for a naturally occurring polypeptide that binds the metallic cation and one monoclonal antibody specific for a metallic cation.

Alternatively, the kit can contain a single type of antibody. For example, the kit can contain an antibody specific for a metallic cation that can be used to detect the amount of lead cation bound by a naturally occurring polypeptide that binds at least two of the metallic cations per polypeptide, as described previously.

Optionally, the kit can contain a capture antibody specific for an enzyme that is inhibited by the metallic cation, and components for measuring the enzyme activity, as described previously. For example, the kit could provide an antibody to ALAD, reagents for restoring the enzyme activity such as EDTA and/or solution containing $Zn^{+2}$ ions and the reagents required to measure ALAD enzyme activity such as δ-amino-levulinic acid.

One of the types of antibodies is preferably immobilized on a solid substrate. Antibodies can be immobilized onto solid substrates by standard methods, as described in *Antibodies: A Laboratory Manual,* cited supra. Suitable solid substrates include materials having a membrane or coating supported by or attached to sticks, cups, flat packs, or other solid supports. Other solid substrates include cell culture plates, ELISA plates, tubes, and polymeric membranes. The preferred solid substrate is a stick coated with a polymeric membrane.

One of the types of antibodies is preferably labelled with a detectable agent, typically the antibody not immobilized on the substrate. Antibodies can be labelled with detectable agents by standard methods, as described in *Antibodies: A Laboratory Manual,* at pages 319–358, cited supra. Suitable detectable agents include enzymes, radioactive labels, fluorochromes, and biotin. The preferred detectable agent for use in the kit is an enzyme, and more preferably, an enzyme that converts a substrate into a color product that can be detected visually.

The kit optionally contains means for detecting the detectable agent. If the antibody is labelled with a radioactive label or a fluorochrome, preferably no means for detecting the agent is provided in the kit. Typically, the consumer will have spectrophotometers, scintillation counters, and microscopes that can be used to detect these detectable agents. If the detectable agent is biotin or an enzyme, means for detecting the detectable agent can be supplied with the kit. Suitable examples of means for detecting the detectable agent include a substrate for the enzyme or avidin. The means for detecting the detectable agent is present in a sufficient concentration to detect substantially all of the second antigen-antibody complex. Preferably, the substrate for the enzyme is provided in a ratio of about 2:1 to 100:1 with the amount of antibody labelled with enzyme present in the kit.

The preferred means for detecting the detectable agent is a substrate that is converted by the enzyme into a colored product. The especially preferred combination of detectable agent and means for detecting the detectable agent is horseradish peroxidase and 2,2'-azino-di-[3-ethyl-benzothiazoline sulfonate] (ABTS).

The kit also optionally contains a lysing agent that functions to lyse cells present in the sample of body fluid. Suitable lysing agents include surfactants such as Tween-80, Nonidet P40, and Triton X-100. Preferably, the lysing agent is immobilized onto the solid substrate along with one of the antibodies.

The kit can also contain a buffer solution for washing of the substrate between steps. The buffer solution is a physiological solution such as a phosphate buffer, physiological saline, citrate buffer, or Tris buffer.

The kit can also include standards containing different concentrations of a metallic cation-naturally occurring polypeptide complex. The standards can be prepared by mixing different amounts of the metallic cation ranging from 0.5 μg/dl to 50 μg/dl with a single concentration of a naturally occurring polypeptide that binds metallic cations. Solutions containing different amounts of a metallic cation-naturally occurring polypeptide complex are then formed and run in the immunoassay methods of the invention.

In a preferred version, each of the standard solutions is contacted with a first type of antibody to form a first antigen-antibody complex. A second type of antibody labelled with a detectable agent is then added to form the second antigen-antibody complex. The amount of second antigen-antibody complex is detected by measuring the amount of detectable agent. The amount of the second antigen-antibody complex is measured for each of the standard solutions and then plotted against the concentration of the metallic cation initially added to each of the standard solutions. In addition, the amount of the metallic cation present in the second antigen-antibody complex can be measured by atomic absorption spectroscopy and the absolute amount of the metallic cation bound to the naturally occurring polypeptide can be compared to the amount of metallic cation initially added and to the amount of the second antigen-antibody complex determined by detecting the detectable agent.

Optionally, one or more of the standards containing the different concentrations of the metallic cation-naturally occurring polypeptide complex can be immobilized onto a portion of the solid substrate. Preferably, three different standards can be immobilized, each in a different portion of the solid substrate. For example, standards containing a naturally occurring polypeptide mixed with 1, 5 and 10 μg/dl can be immobilized onto the solid substrate by binding to the immobilized antibody specific for the naturally occurring polypeptide. A portion of the immobilized solid substrate is available for binding of the test sample of the body fluid. When the immunoassay is completed by conversion of the enzymatic substrate to a colored product, the amount of colored product produced by the test sample of body fluid can then be immediately compared with the amount of colored product produced for each of the standard amounts.

Optionally, the kit can include a card with a visual representation of the amount of colored product produced by a particular amount of a standard containing a naturally occurring polypeptide mixed with a known concentration of the metallic cation. Preferably, the card contains a plurality of different visual representations of the different intensities of colored product associated with the different amounts of the standard concentrations of the metallic cation. This card can be used by the consumer to compare the amount of the colored product produced with the test sample of a body fluid and, thereby, quantitate the amount of metallic cation present in the sample of body fluid.

In a preferred kit, an antibody specific for ALAD is immobilized onto a portion of a dipstick composed of membrane attached to a stick. The antibody specific for ALAD is capable of binding substantially all of the ALAD present in the sample in less than about 10 minutes. The dipstick also has a lysing agent immobilized along with the antibody specific for ALAD, preferably Triton X-100. The preferred kit also contains a phosphate buffer solution and an antibody specific for the lead cation labelled with horseradish peroxidase. The antibody specific for lead cation is preferably an antibody that can detect lead cation in samples of body fluids containing as low as about 1 μg/dl of lead cation. The preferred kit also contains a substrate for horseradish peroxidase, preferably ABTS. The preferred kit also contains a card with a plurality of visual representations of different amounts of colored product formed by conversion of ABTS by horseradish peroxidase for different standard amounts of samples containing the metallic cation.

EXAMPLE I

Preparation of Monoclonal Antibodies Binding to a Metallic Cation Mercury

The strategy for both inducing and selecting metal cation-specific antibodies was to prepare a complex in which the metal ion could be bound as a monodentate ligand. The coordination number of most metals, which denotes the number of ligands attached to the central metal atom in a complex, is generally four to six, although numbers from three to ten have been noted. (D. Craig et al., *Chelating Agents and Metal Chelates*, F. Dwyer and D. Mullon editors, pp. 51–93, Academic Press, NY (1966).) In the complex used in these experiments, mercuric chloride was added to glutathione (GSH), which is a tripeptide of L-γ-glutamyl-cysteinylglycine. The disassociation constant of mercuric ions bound to sulfhydryl groups has been reported to be as high as $10^{-42}$M. Thus, the interaction is sufficiently strong that a stable complex can be formed by interaction of mercury with only the sulfhydryl group of cysteine, without requiring the participation of either the amino or carboxyl groups of the other two amino acids. (B. Fuhr et al., *J. Am. Chem. Soc.*, 95:6944 (1973).)

The immunogen consisted of GSH-HgCl conjugated to a carrier protein keyhole limpet hemocyanin. BALB/c mice were given multiple intraperitoneal injections of the HgCl-GSH-keyhole limpet hemocyanin emulsified in Freund's adjuvant, with a total of 50 μg of protein per injection. The mice were bled after the fifth injection, and their sera were analyzed by ELISA against bovine serum albumin (BSA)-GSH and BSA-GSH-HgCl for evidence of mercury-specific antibodies. The results are shown in Table 1 below.

TABLE 1

Reactivity of Serum from
BALB/c Mice Injected with BSA-glutathione-HgCl

| Mouse # | BSA—GSH | BSA—GSH—HgCl | % Difference |
|---|---|---|---|
| 1 | 1.332 | 1.214 | −8.9 |
| 2 | 0.808 | 0.886 | +9.7 |
| 3 | 2.382 | 1.505 | −36.8 |
| 4 | 0.654 | 0.947 | +44.8 |
| 5 | 0.682 | 0.848 | +24.3 |
| 6 | 0.453 | 0.756 | +66.9 |
| 7 | 0.567 | 0.865 | +52.6 |

TABLE 1-continued

Reactivity of Serum from
BALB/c Mice Injected with BSA-glutathione-HgCl

| Mouse # | BSA—GSH | BSA—GSH—HgCl | % Difference |
|---|---|---|---|
| 8 | 1.670 | 1.456 | −12.8 |
| background | 0.299 | 0.308 | +3.0 |

One hundred microliters of serum was added to the wells of microtiter plates to which either BSA-glutathione or BSA-glutathione-HgCl had been adsorbed. After incubation for 2 hours at room temperature, the plate was washed three times with PBS followed by addition of 100 μl of goat anti-mouse serum. The plate was incubated and washed as above, then 100 μl of rabbit anti-goat serum conjugated with alkaline phosphatase was added. After incubation and washing as above, 100 μl of 2 mM para-nitrophenyl phosphate in 1M diethanolamine, pH-9.6, containing 25 mM $MgCl_2$, was added, and the $A_{405}$ of each well was measured after incubation at room temperature of 15–30 minutes. Percent difference was calculated by the following formula:
Percent difference = [($A_{405}$ of BSA—GSH—Hg − $A_{405}$ of BSA—GSH) ÷ ($A_{405}$ of BSA—GSH)] × 100.
Serum from an unimmunized mouse served as background reactivity for each antigen.

The initial screening for the presence of mercury-specific antibodies in serum was simply higher reactivity with the immunogen containing mercury than with immunogen not containing mercury. Several mice, (e.g., #'s 2, 4, 5, 6, and 7) satisfied this condition.

Mouse #6 was given a booster injection, and its spleen was used for fusion three days later. The ELISA procedure used to screen the hybridoma culture fluids was the same as described in the legend to Table 1.

TABLE 2

Reactivity of Hybridoma Antibodies with
BSA-glutathione-HgCl and BSA-glutathione

| Hybridoma | BSA—GSH—HgCl | BSA—GSH |
|---|---|---|
| 1H11 | 1.246 | 1.202 |
| 2A9 | 0.758 | 1.052 |
| 3A12 | 1.792 | 2.217 |
| 3H9 | 1.606 | 2.134 |
| 1F10 | 1.175 | 0.406 |
| 3E8 | 1.076 | 0.410 |
| 4A10 | 1.104 | 0.400 |
| Neg. control | 0.428 | 0.456 |

Of 134 hybridomas obtained, seven of them demonstrated reactivity consistent with specificity for some part of the GSH-HgCl component of the immunogen (Table 2). MAb's 1H11, 2A9, 3A12, and 3H9 showed a pattern consistent with GSH-specificity, since they reacted with GSH whether $HgCl_2$ was present or not. On the other hand, MAb's 1F10, 3E8, and 4A10 were two- to three-fold above background when assayed with BSA-GSH-HgCl. Background was established for both BSA-GSH and BSA-GSH-HgCl by measuring their reactivities with a dinitrophenol-specific monoclonal antibody.

These results suggested that the latter three antibodies (1F10, 3E8, and 4A10) were specific for either mercuric ions alone or for an epitope consisting of both GSH and $HgCl_2$. Mab's 4A10 (BN No. 4A10B4, ATCC No. HB 10381) and 1F10 were subcloned and analyzed further to determine whether they would react with mercuric chloride by itself. To do so, an inhibition assay was performed in which tenfold dilutions of $HgCl_2$ from $10^{-2}$M to $10^{-11}$M were used to inhibit antibody binding to BSA-GSH-HgCl adsorbed to a microtiter plate.

Figure 1:
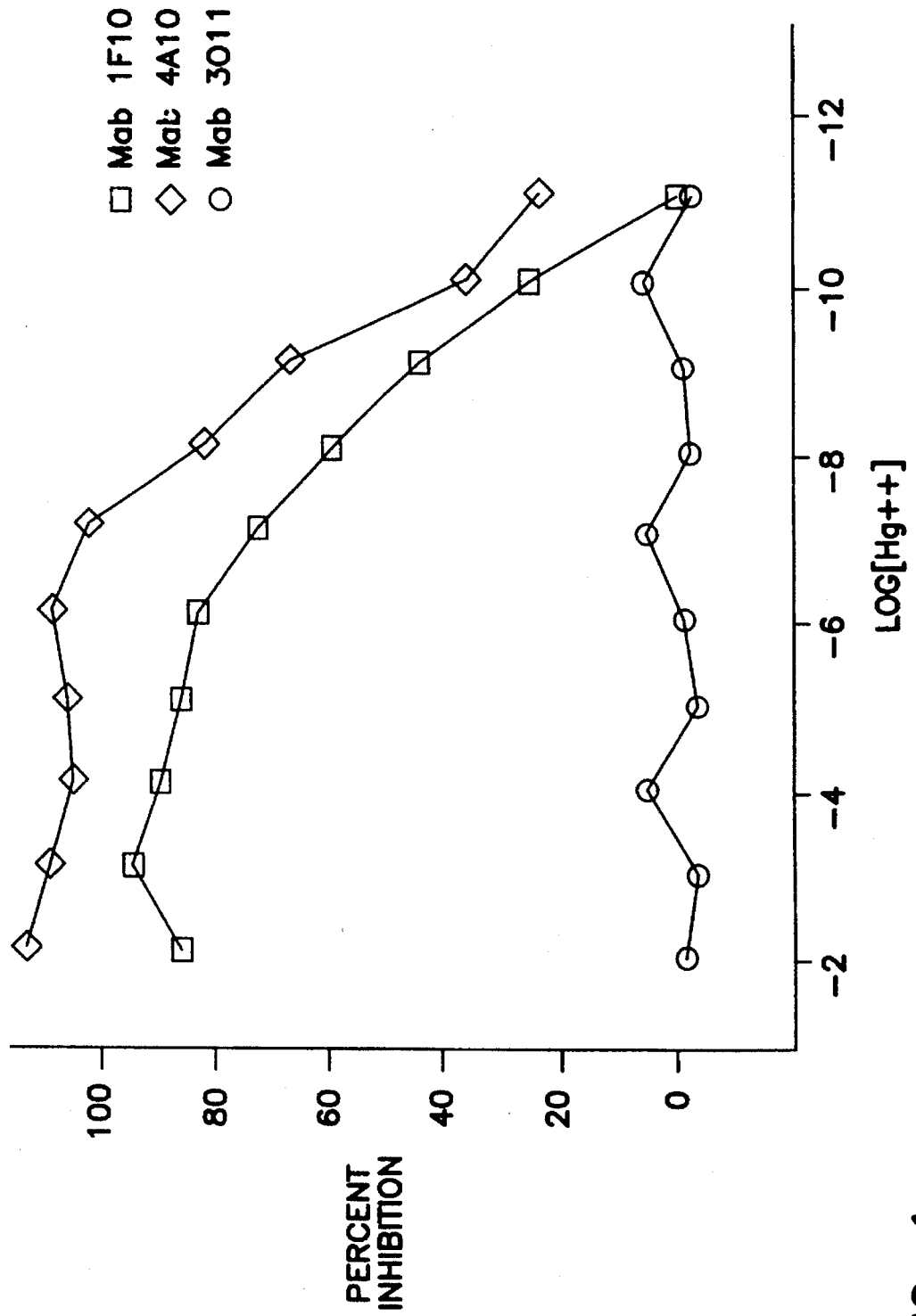
FIG. 1 shows inhibition of binding of mAb 4A10 and mAb 1F10 to immobilized BSA-glutathione-HgCl by soluble mercuric chloride.

The inhibition assay was conducted as follows. Fifty microliters of each concentration of mercuric chloride and 50 µl of diluted ascites fluid containing the indicated antibody were incubated for 30 minutes at room temperature in the wells of a microtiter plate containing adsorbed BSA-glutathione-HgCl. The plates were then washed, and horseradish peroxidase-conjugated goat anti-mouse serum was added. After incubation and washing as above, ABTS substrate was added, and the $A_{405}$ was measured after 15 minutes. Each point represents the average of triplicate determinations. Percent inhibition was calculated according to the following formula:

Percent inhibiton = $(1 - \{[A405$ of exp. $- A405$ of neg$] \div$ $[A405$ of pos. $- A405$ of neg.$]\}) \times 100$ The results are shown in FIG. 1.

The binding of both antibodies to adsorbed antigen was inhibited by soluble $HgCl_2$, with 50% inhibition between $10^{-9}$M and $10^{-10}$M $HgCl_2$ for each. The specificity of the inhibition was demonstrated by the inability of the same concentrations of mercuric chloride to inhibit the binding of an asparagine synthetase-specific monoclonal antibody (MAb 3D11) to asparagine synthetase. These data demonstrated that reactivity of both antibodies with $HgCl_2$ was independent of the presence of either GSH or KLH.

EXAMPLE II

Characterization of the Binding Characteristics of Monoclonal Antibodies to Mercury Clearly, antibodies capable of reacting with soluble mercuric chloride were identified. It was of interest, then, to determine the affinity of the antibodies for mercuric ions, as well as to identify other metals to which they might bind. The other metal salts used for these analyses included barium chloride, cadmium chloride, chromic chloride, copper chloride, ferrous sulfate, gold chloride, mercuric acetate, nickel chloride, selenium oxide, silver chloride, and zinc chloride. The procedure used to determine the affinity of the antibodies for the various metals was the competition ELISA described by Friguet et al. (*J. Immunol. Methods*, 77:305 (1985), which is hereby incorporated by reference.

The results indicated that the disassociation constant of MAb 4A10 for $HgCl_2$ was $2.3\pm0.8\times10^{-9}$M, while that of MAb 1F10 was $3.7\pm1.5\times10^{-9}$M. Neither antibody bound any of the other metals to a detectable extent. However, both antibodies did have a similar affinity for mercuric acetate, with the affinities being $4.1\pm0.1\times10^{-9}$M and $8.2\pm2.5\times10^{-9}$M for 4A10 and 1F10, respectively. These results indicated that the mercuric ion itself was the major epitope recognized by these antibodies, regardless of the counterion originally present in the mercury-containing compound being assayed for antibody reactivity.

Equilibrium dialysis of these monoclonal antibodies with uncomplexed glutathione was conducted and it was determined that the disassociation constant for glutathione was less than $10^{-5}$M. This data further supports the view that these antibodies are immunoreactive with a bare metal cation.

The specificity of the antibodies was further illustrated by their ability to detect mercury at concentrations in the part-per-billion range, even in the presence of other metals. This was demonstrated with an EPA Quality Control (QC) sample containing the following mixture of metals: 0.2 mg/L $Hg^{++}$, 100 mg/L $Ba^{++}$, 1 mg/L $Cd^{++}$, 5 mg/L $Cr^{+++}$, 5 mg/L $Pb^{++}$, and 5 mg/L $Ag^+$. The sample was diluted to known $Hg^{++}$ concentrations, which were then assayed by ELISA and compared to results obtained with a standard consisting of known concentrations of mercury chloride.

Briefly, the ELISA was conducted as follows. The QC sample and $HgCl_2$ were diluted in water to mercury concentrations ranging from 0.5 to 200 ppb, then analyzed by ELISA. A sample containing the same concentration of all other metals as the QC sample except mercury was also included. The absorbance obtained in analysis of both water without added mercury and the EPA sample without mercury was 0.263. Each point represents the average absorbance obtained from quadruplicate analyses of each sample. See FIG. 2.

Figure 2:
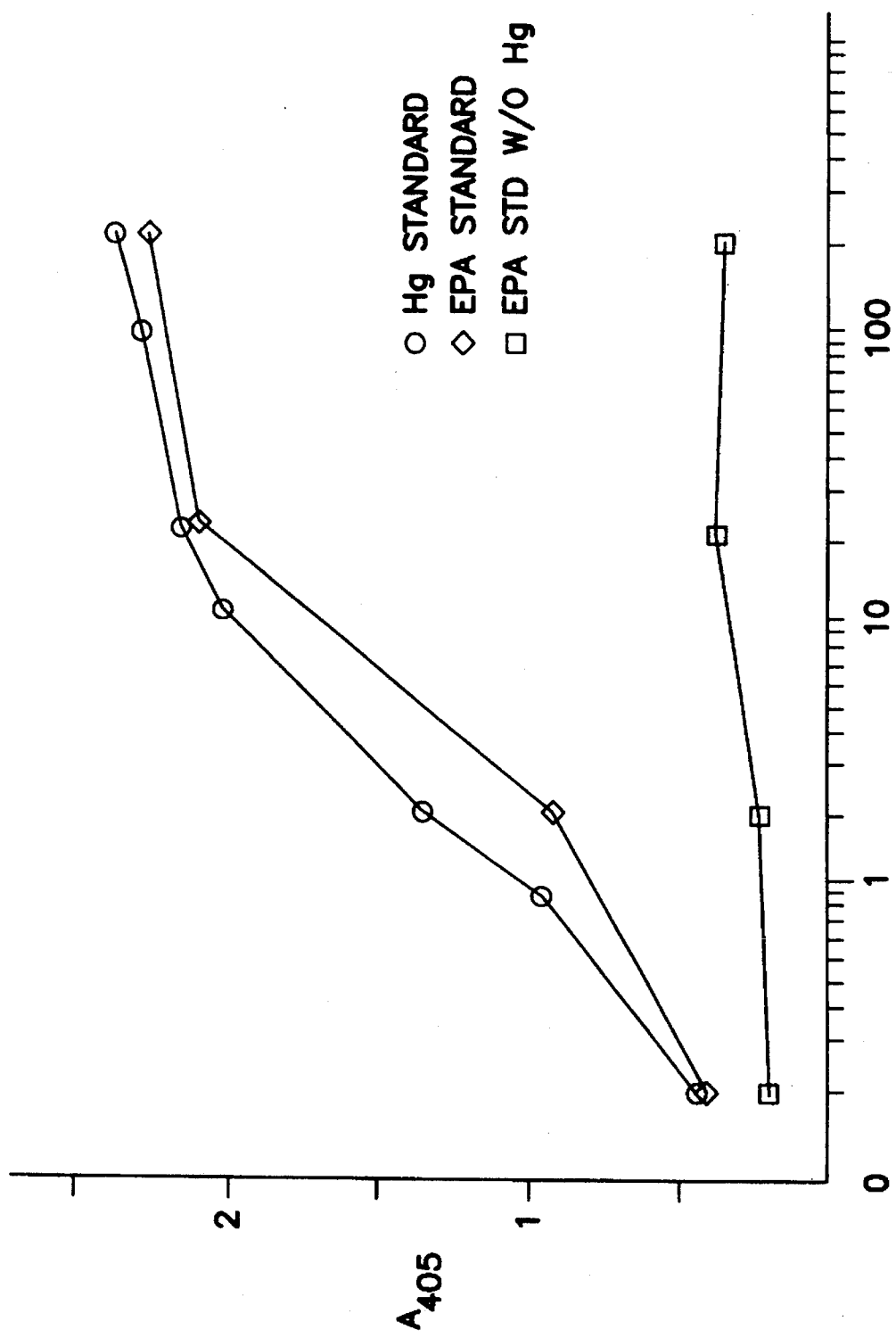
FIG. 2 shows detection of mercury in the EPA Quality Control sample by ELISA.

The results in FIG. 2 show that significant reactivity was obtained with both the EPA sample and the mercury standard at 2 ppb mercury, and the absorbance for both samples was linear up to 20 ppb mercury. Reactivity was due to the presence of mercury and not to recognition of one of the other metals, since a sample containing all of the metals except mercury in the same concentrations as in the EPA sample gave the same absorbance as water containing no mercury.

The results in FIG. 2 clearly demonstrated that the ELISA was capable of sensitive and reproducible detection of mercuric ions in water, but they did not reveal how well the ELISA correlated with atomic absorption. This is an important consideration since cold-vapor atomic absorption is currently the method of choice for mercury determination. To correlate the results obtained from the two methods, an atomic absorption mercury reference standard was diluted in 0.1M HEPES, pH 6.8, to a mercury concentration of 100 ppb. At this point, two aliquots were removed and diluted to the appropriate concentrations for immunoassay in HEPES or for atomic absorption in 10% nitric acid. Samples containing 0, 2, 4, 5, 10 and 15 ppb mercury were then analyzed by both methods. The values shown represent the mean and one standard deviation of quadruplicate analyses by immunoassay and triplicate analyses by atomic absorption. (See FIG. 3.)

Figure 3:
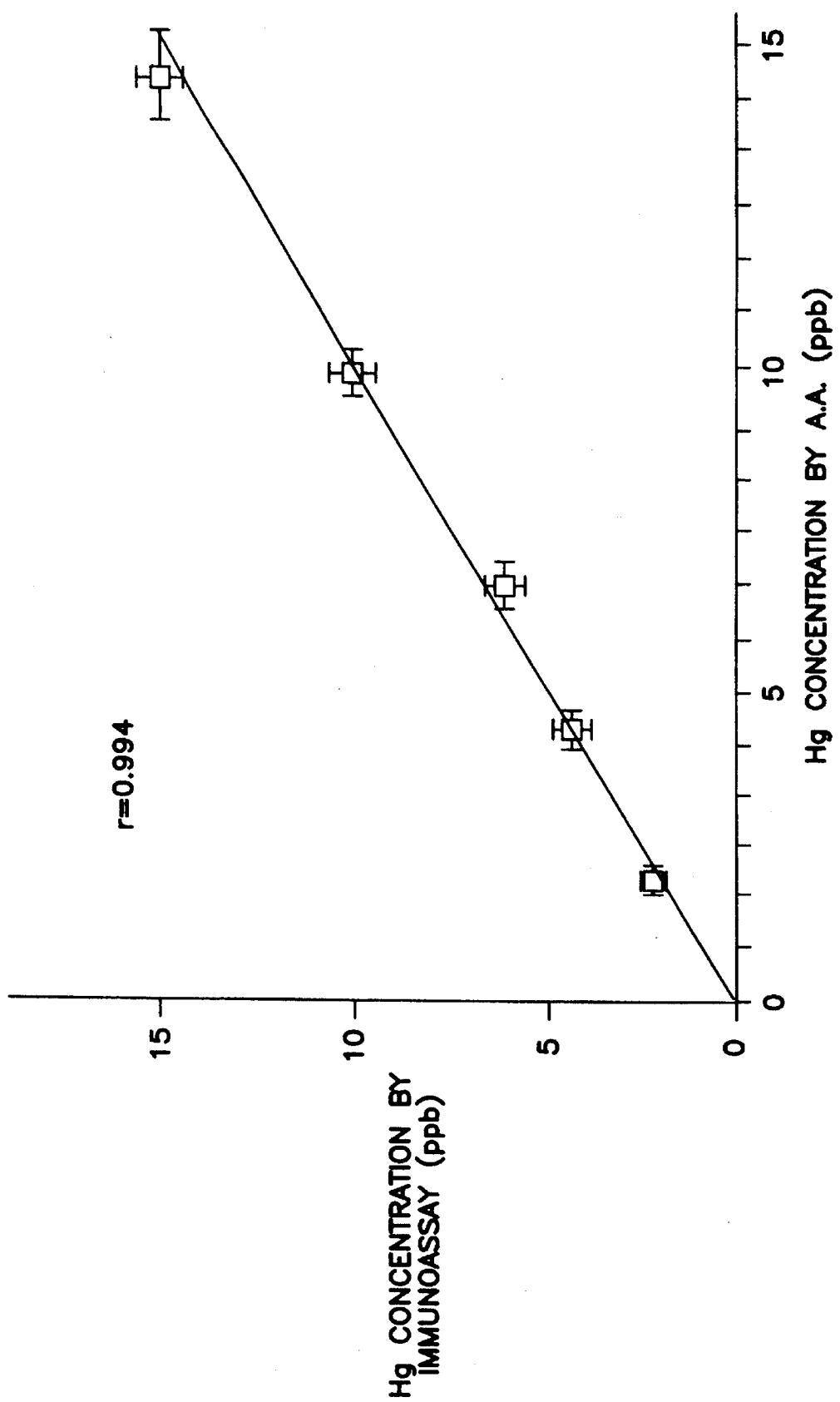
FIG. 3 shows a comparison of mercury detection by ELISA and atomic absorption.

As shown in FIG. 3, the results obtained from the two methods were in close agreement, as indicated by a correlation coefficient of >0.99. In addition, the standard deviation of the immunoassay at most mercury concentrations was the same or less than that obtained by atomic absorption. These results indicated that, under the conditions of this assay, quantitation of mercury by ELISA was as precise as cold-vapor atomic absorption.

EXAMPLE III

Production of Monoclonal Antibodies to a Lead Cation

The same strategy used for production of mercury-specific antibodies employing immunization of mice with a metal cation-spacer arm carrier has now been applied to generation of antibodies specific for lead. Initially, seven antibodies were identified that reacted with a carrier protein only when lead was present. The ELISA results obtained from screening these antibodies are shown below.

| Hybridoma | BSA—GSH | BSA—GSH—Pb |
|---|---|---|
| 6B11 | 0.298 | 0.954 |
| 8E7 | 0.055 | 0.987 |
| 4E8 | 0.195 | 0.618 |
| 3B8 | 0.212 | 0.975 |
| 9D3 | 0.191 | 0.584 |
| 3B7 | 0.074 | 0.710 |
| 1C3 | 0.161 | 1.560 |

Several of these antibodies have been assayed for detection of lead bound to other carriers, such as other globular proteins like ovalbumin, or synthetic polypeptides such as poly-L-lysine.

A monoclonal antibody specific for lead cation can have a disassociation constant for lead cation of less than $10^{-9}$M and does not appreciably bind to cadmium, copper, zinc, mercury, nickel, and cobalt cations to any appreciable extent.

Figure 4:
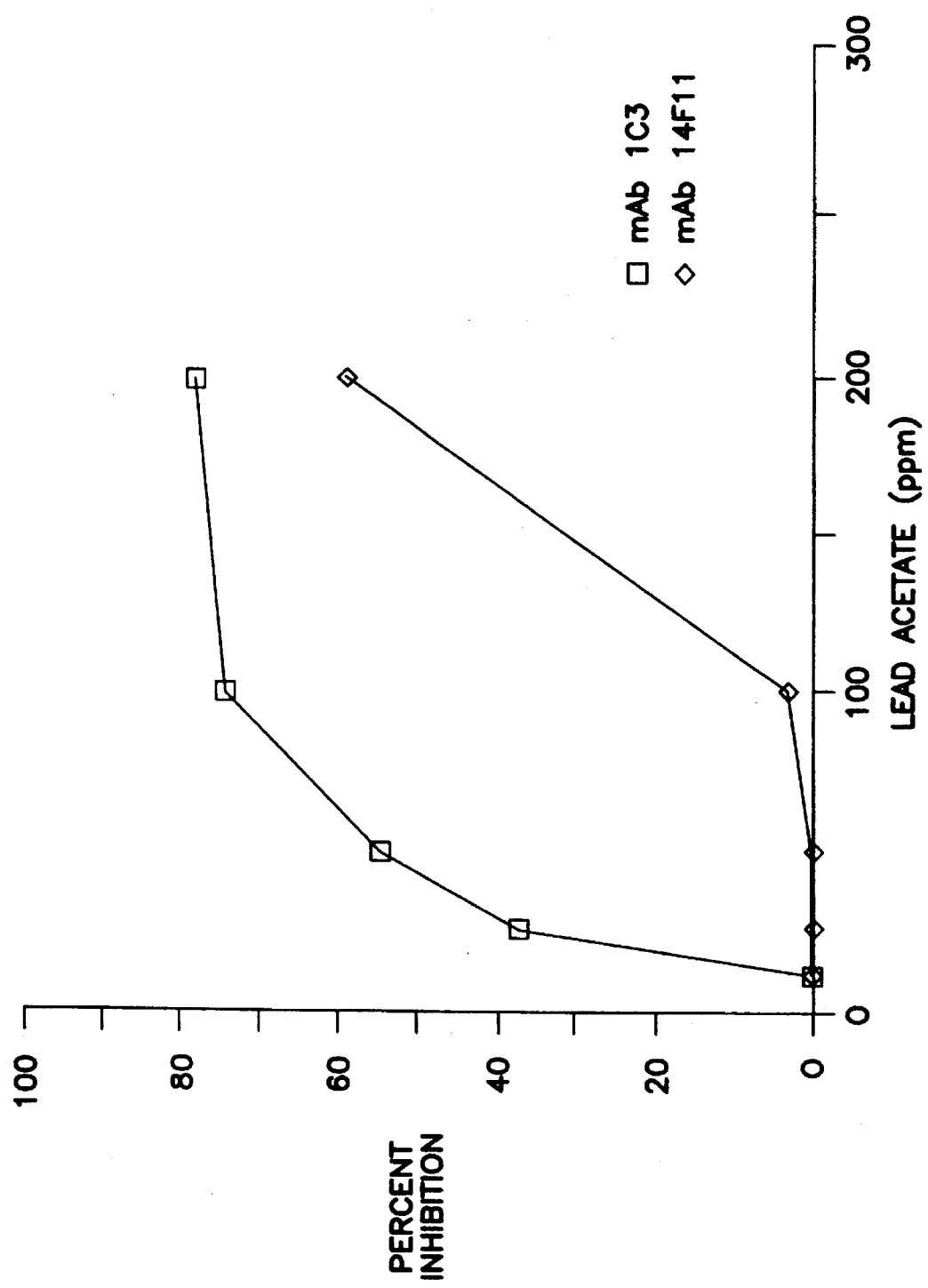
FIG. 4 shows inhibition of binding of mAb 1C3 and mAb 14F11 to immobilized BSA-glutathione $Pb^{+2}$ by soluble lead acetate.

To determine whether any of these antibodies would bind lead in solution, mAb's 1C3 and 14F11 (prepared as described in Example IV) were used in competition assays as described in Example I, to see if lead nitrate in solution would inhibit the binding of either mAb to BSA-GSH-Pb$^{++}$ adsorbed to a solid phase. Briefly, 50 μl of each concentration of lead acetate and 50 μl of diluted ascites fluid containing the indicated antibody were incubated for 30 minutes at room temperature in the wells of a microtiter plate containing adsorbed BSA-glutathione-lead acetate. The plates were then washed, and horseradish peroxidase-conjugated goat anti-mouse serum was added. After incubation and washing as above, ABTS substrate was added, and the $A_{405}$ was measured after 15 minutes. Each point represents the average of quadruplicate determinations. Percent inhibition was determined according to the formula in the legend to FIG. 1. The results are shown in FIG. 4.

The binding of both 1C3 and 14F11 is inhibited by soluble lead acetate at concentrations ranging from 10 to 100 ppm, with 50% inhibition at approximately 20 ppm and 150 ppm for mAb's 1C3 and 14F11, respectively. Thus, these two antibodies, in addition to reacting with lead attached to a carrier, also react with lead in solution.

EXAMPLE IV

Preparation of Monoclonal Antibodies Specific for Pb-ALAD

Monoclonal antibodies specific for Pb-ALAD were prepared by standard methods. The amount of ALAD complexed with Pb is a sensitive indicator of the toxicity of the lead contamination. ALAD is a naturally occurring enzyme whose activity is inhibited by lead contamination and this inhibition represents one of the toxic effects of lead contamination. The amount of Pb-ALAD present in the blood sample is a good indicator of the toxicity level associated with the lead contamination of the patient.

A monoclonal antibody to Pb-ALAD was prepared as described in Example I. The resulting hybridomas were screened for immunoreactivity with Pb-ALAD and ALAD.

A monoclonal antibody, designated 14F11, has been produced by injection of Pb-ALAD. The ELISA results when this antibody and antibody IC3 (prepared as described in Example III) were tested with ALAD-Pb and ALAD alone are shown below:

| Hybridoma | ALAD—Pb | ALAD |
|---|---|---|
| 14F11 | 0.751 | 0.050 |
|  | 1.813 | 0.048 |
| 1C3 | 1.586 | 0.030 |

These antibodies are specific for an epitope on the ALAD-lead complex and do not react with epitopes on ALAD alone.

The results shown above clearly demonstrate that the same condition that was found for mercury also exists for lead, namely that antibodies can be produced that recognize lead when it is either in solution or attached to a carrier. Monoclonal antibody 14F11 could detect lead in solution at 10 ppm and 1C3 could detect lead at 1 ppm. Monoclonal antibodies reactive with ALAD bound to lead and non-crossreactive with ALAD alone can be used in an assay to detect the amount of lead present in a blood sample.

The immunoreactivity of monoclonal antibodies 14F11 and 1C3 with bovine ALAD complexed to other metal cation was also tested. Bovine ALAD was incubated with 1 mM of metal cations including Pb, Zn, Cu, Cd, Ni, and Hg, for 60 minutes. The bovine-ALAD metal complexes were then placed in an ELISA well and assayed for the ability to bind monoclonal antibodies 14F11 and 1C3. The results are shown below.

| Metal Ion | 14F11 |
|---|---|
| Pb$^{+2}$ | 0.638 |
| Zn$^{+2}$ | 0.060 |
| Control | 0.076 |
| Pb$^{+2}$ | 0.908 |
| Cu$^{+2}$ | 0.102 |
| Control | 0.070 |
| Cd$^{+2}$ | 0.135 |
| Ni$^{+2}$ | 0.126 |
| Hg$^{+2}$ | 0.590 |
| Control | 0.128 |

| Metal Ion | 1C3 |
|---|---|
| Pb$^{+2}$ | 0.413 |
| Hg$^{+2}$ | 0.150 |
| Cd$^{+2}$ | 0.064 |
| Control | 0.064 |

EXAMPLE V

Production of Hybridoma Antibodies Specific for ALAD

Since ALAD is one of the earliest and most sensitive indicators of exposure to lead, it is a logical target for determination of the lead burden in an individual. ALAD is a large, multimeric protein, so it will induce formation of high affinity, specific monoclonal antibodies. The ALAD-specific antibody can be used to capture the enzyme from a sample of body fluid for subsequent detection of lead bound to it.

The injection regimen for production of antibodies specific for ALAD was as follows. Bovine liver ALAD was mixed with adjuvant and injected intraperitoneally into BALB/c mice. Each mouse was given three injections with 50 μg of ALAD per injection. The presence of ALAD-specific antibodies was monitored by an ELISA in which 200 μl of ALAD at a concentration of 5 μg/ml is adsorbed to the wells of 96-well polystyrene microtiter plates by incubation at room temperature for 2 hours. Two hundred microliters of 1% polyvinyl alcohol in PBS was added to each well and incubated at room temperature for one hour to block the nonspecific protein-binding sites. Fourfold dilutions of each serum sample were prepared, and 100 µl of each was added to duplicate wells of a microtiter plate. After incubation at room temperature for 60 minutes, the plates were washed three times with ELISA wash (PBS with 0.1% Nonidet P-40). One hundred microliters of goat anti-mouse serum conjugated to horseradish peroxidase was added, and the plates were incubated and washed as above. Peroxidase substrate (ABTS) was then added, and the absorbance of each well at 405 nm was measured after incubation for 15 minutes at room temperature. Controls consist of assaying each serum dilution against bovine serum albumin instead of ALAD to determine their nonspecific reactivity, and assaying serum from a non-injected mouse against ALAD. Three mice injected as described above show an ELISA titer of >10,000 against ALAD and <1,000 against BSA.

The spleen from one of these mice was used for fusion with SP2/0 myeloma cells for production of hybridomas, according to standard methodology, as described by J. Liddell et al., in *A Practical Guide to Monoclonal Antibodies*, pp. 67–88 (1992). Four monoclonal antibodies were obtained from the fusion. The ELISA results from initial screening of these antibodies against ALAD and BSA-GSH are shown below. BSA-GSH was included to identify polyreactive antibodies.

| Hybridoma | ALAD | BSA—GSH | S/N* |
|---|---|---|---|
| 1C6 | 1.466 | 0.128 | 11.5 |
| 10G4 | 0.796 | 0.109 | 7.3 |
| 11B12 | 1.938 | 0.213 | 9.1 |
| 12F8 | 1.417 | 0.131 | 10.8 |

*S/N = Signal-to-Noise Ratio. This was obtained by dividing the adsorbance with ALAD by that obtained from assay against BSA—GSH.

The results shown above indicate that these four antibodies were specific for ALAD, as indicated by their preferential reactivity with the specific antigen (ALAD) over a nonspecific one (BSA-GSH). However, the ALAD-specific antibodies were induced by injection of bovine liver ALAD and were identified by reactivity with the same immunogen adsorbed to the wells of a microtiter plate. It was possible, then, that the antibodies were specific for a species-specific epitope accessible only when ALAD was adsorbed to a microtiter plate. Adsorption of proteins to a solid support can cause denaturation, so that any monoclonal antibody detected in this assay might be specific for a denatured epitope and would not react with the native enzyme. In addition to recognizing native ALAD in an erythrocyte lysate, an ALAD-specific antibody preferably fulfilled two additional requirements: first, it had to recognize an ALAD epitope whose ability to react with the antibody would not be influenced by the presence of lead; and, second, it had to bind a sufficient amount of ALAD to allow immunological detection of any attached lead. The ability of each of the ALAD-specific antibodies shown above to fulfill these requirements was examined.

To determine whether any of the antibodies would bind ALAD with lead attached, ALAD was adsorbed to the wells, after which Pb was added to some wells but not to others. MAb 11B12 was then tested for reactivity with ALAD in the presence and absence of lead. This antibody was selected because it consistently reacted more strongly with ALAD in routine ELISA's than the other antibodies. The results are shown below.

| Hybridoma | ALAD | ALAD—Pb |
|---|---|---|
| 11B12 | 0.877 | 0.666 |

These results demonstrate that mAb 11B12 reacted with ALAD regardless of the presence of lead.

To assay for antibody binding to human erythrocyte ALAD, inhibition of the enzyme activity in the presence of the monoclonal antibody was measured. The appropriate amount of each antibody was pre-determined by titration in a solid-phase ELISA and added to the wells of a microliter plate. After antibody adsorption to the plate, 100 µl of a lysate from washed human erythrocytes was added. The plates were incubated at room temperature for 30 minutes, washed, and ALAD activity was determined by a modification of the procedure of Tsukamoto et al., *BBA*, 570:167–168 (1979). Briefly, 100 µl of Tris-acetate, pH 7.1, containing 4 mM δ-aminolevulinic acid hydrochloride was added and the plates were incubated at 37° C. for various times. At the appropriate time, 100 µl of Ehrlich's reagent was added, and the reaction mixture was incubated for 30 minutes at room temperature to allow for color development. The absorbance at 540 nm was then determined to measure porphobilinogen synthesis. The results obtained after incubation of the reaction mixture for 48 hours are shown below.

| Hybridoma | Enzyme | Substrate | $A_{450}$ |
|---|---|---|---|
| 11B12 | + | + | 2.066 |
|  | + | − | .065 |
|  | − | + | .026 |
|  | − | − | .027 |

The numbers represent the absorbance at 540 nm in the experimental samples, which contained the reaction mixture described above. The controls consisted of the absorbance at 540 nm obtained with a sample incubated for the same length of time in the absence of monoclonal antibody, or in the absence of enzyme, or in the absence of substrate. The results indicated that 11B12 was suited for trapping enzymatically active ALAD in human erythrocyte lysates.

Monoclonal antibodies that react only with lead-ALAD, as described in Example IV, and not with ALAD can also be selected and used to provide for greater sensitivity.

EXAMPLE VI

Development of an Immunoassay for the Detection of Metallic Cation in a Sample of Body Fluid A method for detecting a metallic cation in a sample of body fluid was developed by detecting the amount of the metallic cation bound to a naturally occurring protein such as ALAD present in the sample of body fluid. Two antibodies specific for ALAD, prepared as described in Example IV, were used to determine whether lead could be detected in blood samples in the assay design envisioned for the kit format. The blood samples used for this experiment were bovine blood samples from cattle exposed to lead, which were obtained from the Center for Disease Control.

MAb 11B12 (ALAD-specific) was adsorbed to the wells of a microtiter plated as described above. One hundred microliters of extract containing ALAD from two blood samples from cows exposed to lead. The two samples were designated BE590, which contained lead at 8.5 µg/dl and BE890, which contained lead at a concentration of 15 μg/dl. After incubation for 30 minutes in the well, the extract was removed, the plates were washed, and 100 μl of a 1:1000 dilution of ascites fluid containing mAb 14F11 (lead-specific) or 10G4 (ALAD-specific) was added. After incubation for 60 minutes, a peroxidase labelled anti-IgM antibody was added to each well. After incubation and washing as above, 100 μl of ABTS was added, and the absorbance of 405 nm was measured. The results are shown below.

| Blood Sample | 10G4 Absorbance | 14F11 Absorbance |
| --- | --- | --- |
| PBS | 0.195 | 1.091 |
| BE590 | 1.452 | 1.195 |
| BE890 | 1.451 | 1.405 |

The numbers represent the absorbance at 405 nm of the samples in the ELISA done as described above. The sample designated as PBS served as a negative control and contained only PBS instead of extract from a blood sample.

As can be seen, Pb was detected in the contaminated samples using the immunoassay in accordance with the invention. These results are extremely important because they indicate that the approach described for detecting lead bound to ALAD will do so in a "real world" blood sample. In spite of the seeming lack of sensitivity of mAb 14F11 for binding to soluble lead (FIG. 4), it is sufficiently sensitive to be used for detecting lead bound to ALAD. As previously mentioned, it could be that, since this mAb was induced by Pb-ALAD, it will react with soluble lead, but preferably reacts with lead bound to ALAD.

EXAMPLE VII

Detecting Lead Bound to Hemoglobin

Lead binds to many of the proteins found in blood cells and plasma. Hemoglobin, a major constituent of erythrocytes, is one of the proteins that binds lead. Gercken et al., *Anal. Chem.*, 63:283–287 (1991). An immunoassay that uses antibodies to hemoglobin and antibodies to lead might specifically detect lead or mercury bound to hemoglobin.

Antibodies to hemoglobin are generated easily using standard laboratory animals, and also are available commercially. These antibodies may be polyclonal or monoclonal, and can be very specific, e.g. for rare variants or for specific subunits or for one species, or can be less specific and more crossreactive. Antibodies to lead have also been generated as described in Example III.

Immunoassays to detect lead bound to hemoglobin have been done. First, monoclonal antibodies to hemoglobin (obtained from Medix Biotech, Inc.) were adsorbed to a solid substrate. Next, agents to block non-specific adsorption were incubated on the solid substrate. Third, samples of lysed erythrocytes from lead contaminated human blood were incubated on the solid substrate. Fourth, a monoclonal antibody specific for lead (14F11) was incubated on the solid substrate. This was followed by a reporter enzyme conjugated with a chromogenic enzyme substrate. The amount of lead present in the original sample should positively correlate with the amount of color produced.

The results show that lead bound to hemoglobin was detected using an immunoassay employing two different antibodies as described in Example VI:

| Sample | Adsorbance | Blood-Pb |
| --- | --- | --- |
| 1 | 1.291 | 55 |
| 2 | 0.225 | 4 |
| 3 | 0.244 | 2 |
| 1X PBS | 0.093 | 0 |

There is a good positive correlation between adsorbance and blood-lead values. Thus, immunoassays for lead bound to hemoglobin can be used as an indication of a patient's lead burden.

EXAMPLE VIII

Detecting Lead Bound to Serum Albumin

Lead binds to many of the proteins found in blood cells and plasma. Serum albumin, a major constituent of serum, is one of the proteins that also binds lead. An immunoassay that uses antibodies to serum albumin and antibodies to lead can specifically detect lead bound to serum albumin.

Antibodies to serum albumin are generated easily using standard laboratory animals, and also are available commercially. These antibodies may be polyclonal or monoclonal, and can be very specific, e.g. for rare variants or for specific epitopes or for one species, or can be less specific and more crossreactive. Antibodies to lead have been generated as described in Example III.

Immunoassays to detect lead bound to serum albumin have been done. First, antibodies to serum albumin (Sigma Chemical Co., St. Louis, Mo.) were adsorbed to a solid substrate. Next, agents to block non-specific adsorption were incubated on the solid substrate. Third, samples of lead contaminated human serum were incubated on the solid substrate. Fourth, a monoclonal antibody specific for lead (14F11) was incubated on the solid substrate. This was followed by incubation with an antibody reporter enzyme conjugated antibodies that bind to the lead antibodies conjugated to a reporter enzyme, and then followed by a chromogenic enzyme substrate.

The results show that lead bound to serum albumin was detected in an immunoassay using two different antibodies as described in Example VI.

| Sample | Adsorbance | Blood-Pb |
| --- | --- | --- |
| 1 | 1.251 | 35 |
| 2 | 0.390 | 20 |
| 3 | 0.442 | 16 |
| 4 | 0.400 | 12 |
| 5 | 0.352 | 4 |
| 1X PBS | 0.093 | 0 |

This immunoassay is useful to qualitatively screen for the presence or absence of Pb contamination of a blood sample.

EXAMPLE IX

Comparison of an Acute vs. Chronic Lead Exposure on the Detection of Pb Bound to ALAD and Hemoglobin Naturally occurring proteins that bind to lead can also serve as indicators of an acute vs. chronic exposure to lead. For example, it is known that inhibition of ALAD activity with $Pb^{+2}$ after a single exposure in mice occurs as early as 3 hours and peaks in 24 hours and then the ALAD activity returns to normal activity within 2–4 days post-exposure. Schlick et al., *Arch. Toxicol.*, 43:213 (1980). Binding of $Pb^{+2}$ to hemoglobin may proceed more slowly and Pb may be retained by hemoglobin for a longer period of time. An immunoassay employing a comparison of lead bound to ALAD and to hemoglobin may allow diagnosis of an acute vs. chronic exposure to $Pb^{+2}$.

Rabbits will be exposed to an acute and chronic Pb exposure in their drinking water and Pb concentration bound to ALAD and hemoglobin determined over time. Lead acetate will be administered to the animals in water bottles. Sodium acetate will be fed to control animals. The treatment groups will be as follows:

Treatment 1 (2 to 4 rabbits)
  Treatment with 10 mg Pb/kg/day for 5 days, followed by control treatment for 5 weeks.
Treatment 2 (2 to 4 rabbits)
  Control treatment for 5 weeks followed by 5 days of 10 mg Pb/kg/day.
Treatment 3 (2 to 4 rabbits)
  Treatment of rabbits with 1 mg Pb/kg/day for 6 weeks.
Treatment 4 (2 to 4 rabbits)
  Control treatment for 6 weeks.

Blood samples will be taken on the first day of treatment every 3 hours and analyzed for Pb bound to ALAD, as described in Example VI, and for Pb bound to hemoglobin, as described in Example VII. Thereafter blood samples will be taken regularly, typically once a week or less, and analyzed similarly. It is likely that the ratio of the amount of Pb detected bound to ALAD compared to the amount bound to hemoglobin after an acute exposure will be higher than the ratio of the amount of Pb detected bound to ALAD compared to the amount bound to hemoglobin after a chronic exposure. It is expected that the amount of lead bound to ALAD will be higher than the amount of lead bound to hemoglobin after an acute exposure. It is expected that the amount of lead bound to ALAD will decrease over time in a chronic exposure as compared to an acute exposure.

EXAMPLE X

Method for Identifying Naturally Occurring Polypeptides That Bind Metallic Cations Naturally occurring polypeptides beside ALAD are capable of binding to metallic cations and can be used to detect the presence of and/or to quantitative the amount of a metallic cation in a body fluid. A method for identifying other naturally occurring polypeptides that bind to metallic cations and/or to identify whether the polypeptides bind metallic cations at a low enough concentration to be a sensitive indicator of metallic cation contamination includes using a Western blot technique. The Western blot technique is carried out according to standard methods, as described in *Antibodies: A Laboratory Manual*, Harlow & Lane, editors, Cold Spring Harbor, Cold Spring, N.Y. at pages 571–610 (1988).

First, blood samples not thought to be heavily contaminated with exogenous metallic cations, such as lead or mercury or methylmercury, were treated with a lysing agent such as Triton X-100. The lysing agent acts to lyse cells, including red cells present in the blood sample. The samples run on Western blots had known concentrations of blood lead determined by anodic stripping voltametry ranging from 4 µg/dl to 55 µg/dl. The samples were then mixed with 4 X sample buffer of 76.0 mg Tris base, 2 gm SDS (sodium dodecylsulfate), 10 ml glycerol, 5 ml β-mercaptoethanol, and distilled $H_2O$ to 25 mls (pH=6.8). Each sample contained a metal containing red cell lysate (varying amounts), 10 µl of 4 X sample buffer and 40 µl distilled $H_2O$. The samples were mixed vigorously and boiled for 5 minutes. Samples were loaded onto Tris/glycine SDS polyacrylamide gels and the gels were electrophoresed under standard conditions as described in *Antibodies: A Laboratory Manual*, cited supra.

Once electrophoresis was completed, the proteins in the samples were transferred to nitrocellulose membranes by either simple diffusion, vacuum assisted solvent flow, or electrophoretic elution. The preferred method is electrophoretic elution by semi-dry transfer. With the semi-dry transfer method, the gel nitrocellulose membrane sandwich was placed between absorbent paper soaked in transfer buffer. The transfer buffer contained 48 mM of Tris base, 2M glycine, 3% methanol, and distilled water. On the bottom plate of the gel transfer apparatus (the anode), the sandwich for electroelution was assembled as follows: a sponge, 3 layers of absorbent paper soaked in transfer buffer, the polyacrylamide gel wetted with $H_2O$, nitrocellulose membrane soaked in water, and 3 layers of absorbent paper soaked in transfer buffer, sponge, and the upper electrode (cathode) on top of the stack. The electrodes were connected and current was applied for 40 minutes at 100 V.

Once transferred to the nitrocellulose membrane, the proteins were reacted with specific antibodies. Before the membrane was treated with the antibodies, however, non-specific binding of the antibody was blocked by treating the membrane with a protein or detergent solution, such as non-fat dry milk. The membranes were then incubated with monoclonal antibodies specific for the metallic cations.

Each membrane was removed from the blocking solution and washed twice for 30 minutes each in PBS. The monoclonal antibody 14F11 specific for lead was incubated with each of the membranes in 1% polyvinyl acetate, 5% bovine calf serum, 0.01% sodium azide in phosphate buffered saline in a shallow tray. Antibody concentration should be between 1–50 µg/ml. The membranes were incubated for at least 2 hours at room temperature with agitation. After incubation, the membrane is washed twice with PBS and twice with ELISA wash (PBS with 0.1% Tritonx-100).

The membrane was then treated with a enzyme labelled secondary antibody. The secondary antibody is a goat anti-mouse IgM antibody labelled with horseradish peroxidase. The membrane and the secondary antibody were incubated for 1.5 hours at room temperature with agitation. The gel was then rinsed twice for 30 minutes with PBS and twice for 30 minutes with ELISA wash. To develop the membrane, the membrane was incubated with the peroxidase substrate TM Blue (TSI, Inc.).

The results are shown in FIG. 5. Lead bound to hemoglobin was detected as shown in Lanes 3, 4 and 5 in blood samples containing as low as 5 µg Pb/dl. The hemoglobin band is seen at 64,000 daltons. Other bands visualized represent carbonic anhydrase (29,000), albumin (66,000), transferrins (76,000–81,000), and hemocyanin (70,000). Lane 2 represents a Western blot of a lead depleted red cell lysate sample. These results show that naturally occurring metallic cation containing proteins can be readily identified using the metallic cation specific antibodies of the invention and Western blot.

Bands identified by Western blot can be identified by their molecular weights, and these bands can be eluted from companion gels for further characterization and identification by methods known to those of skill in the art. For example, a naturally occurring polypeptide binding metallic cations can be identified by using monoclonal antibodies specific for known blood polypeptides. Membranes run under the same conditions can be incubated with monoclonal antibodies specific for human serum albumin or hemoglobin or other known blood proteins.

By comparing the Western blot results for blood samples mixed with different concentrations of the metallic cations, those polypeptides detected as binding lead or mercury at very low concentrations (less than about 25 μg/dl) can be considered sensitive enough to use in a immunoassay for metallic cations. It can also be determined if the binding of the metallic cation by the polypeptide is related linearly to the amount of metallic cation initially added to the sample.

EXAMPLE XI

Formation of Monoclonal Antibodies to Glutathione or Glutathione Metallic Cation Complex Monoclonal antibodies specific for glutathione or glutathione-mercury complex were obtained by following the immunization procedure described in Example I. As shown in Table 2 on page 35, monoclonal antibodies reactive with both glutathione HgCl and glutathione complexed to the carrier bovine serum albumin were isolated and identified in an ELISA assay. Monoclonal antibodies 1H11, 2A9 was specific for both BAS-GSH-HgCl and BSA-GSH. Monoclonal antibodies 3A12 and 3H9 bound to BSA-GSH preferentially, rather than to the BAS-GSH-HgCl. The monoclonal antibodies can be further characterized to ensure that they are specific for the glutathione-mercury complex or glutathione and not for epitopes on BSA.

Monoclonal antibodies 1H11 and 2A9, 3A12 and 3H9 can be assayed in an ELISA for the ability to bind to glutathione alone or glutathione-mercury complex. Briefly, glutathione or glutathione mercury complex can be incubated in the wells of an ELISA plate under conditions that allow the glutathione or glutathione complex to bind to the plate. The ELISA plate is then washed and incubated with either 1H11, 2A9, 3A12, or 3H9 for 2 hours at room temperature. After incubation, the plate was washed and incubated with goat anti-mouse antibody conjugated with alkaline phosphatase. After incubation, paranitrophenyl phosphate is added and A405 of each well measured after incubation at room temperature of 15–30 minutes. The specificity of each of these monoclonal antibodies for either glutathione or glutathione mercury complex can be confirmed by detecting immunoreactivity in the ELISA assay.

Monoclonal antibodies specific for glutathione or glutathione mercury cations can serve as the antibody specific for a naturally occurring polypeptide that binds metallic cation or the antibody specific for an epitope on a metallic cation-naturally occurring polypeptide complex. If the antibody is specific for both glutathione and glutathione mercury complex, it can be used as an antibody specific for a naturally occurring polypeptide that binds metallic cation. If the antibody is only specific for glutathione mercury complex, then it can be used for an antibody specific for an epitope on a metallic cation-naturally occurring polypeptide complex.

All patents and publications cited herein are hereby incorporated by reference. While the present invention has been described in connection with the preferred embodiment thereof, it will be understood many modifications will be readily apparent to those skilled in the art, and this application is intended to cover any adaptations or variations thereof.

What is claimed is:

1. A method for detecting a metallic cation in a sample of a body fluid of an animal, which comprises:

contacting an effective amount of a first antibody specific for a naturally occurring polypeptide or a functional portion of the polypeptide with the sample of body fluid containing the metallic cation to form a first antigen-antibody complex, wherein the naturally occurring polypeptide can bind the metallic cation;

adding an effective amount of a second antibody specific for the metallic cation to the first antigen-antibody complex to form a second antigen-antibody complex; and determining the amount of the metallic cation in the sample of the body fluid by detecting the amount of the second antigen-antibody complex.

2. A method according to claim 1, wherein the second antibody specific for the metallic cation is a monoclonal antibody specific for metallic cation is selected from the group consisting of transition metals, Group IIIa metal/metalloids, and Group IVa metal/metalloids.

3. The method according to claim 2, wherein the metallic cation is lead.

4. A method according to claim 1, wherein the second antibody specific for the metallic cation does not substantially cross-react with other metallic cations.

5. A method according to claim 1, wherein the second antibody specific for the metallic cation has a dissociation constant of about $10^{-4}$ to $10^{-13}$.

6. A method according to claim 1, wherein the second antibody specific for the metallic cation is labelled with an enzyme.

7. A method for determining whether an animal has been exposed acutely or chronically to a metallic cation, which comprises:

detecting the amount of the metallic cation bound to a first type of naturally occurring polypeptide that binds the metallic cation, wherein the first type of naturally occurring polypeptide can bind the metallic cation upon an acute exposure to the metallic cation;

detecting the amount of the metallic cation bound to one or more second type of naturally occurring polypeptide that can bind the metallic cation; wherein the second type of naturally occurring polypeptide can bind the metallic cation after a chronic exposure to the metallic cation and comparing the amount of the metallic cation bound to the first type of naturally occurring polypeptide to the amount of metallic cation bound to one or more second type of naturally occurring polypeptide to determine whether the exposure to the metallic cation is acute or chronic.

8. The method according to claim 7, wherein the first type of naturally occurring polypeptide is ALAD and the metallic cation is lead.

9. The method according to claim 7, wherein the second type of naturally occurring polypeptide is hemoglobin and the metallic cation is lead.

10. The method according to claim 7, wherein the step of detecting the amount of the metallic cation bound to a first type of naturally occurring polypeptide includes contacting an effective amount of a first antibody specific for the first type of naturally occurring polypeptide with the sample of body fluid containing the metallic cation to form a first antigen-antibody complex;

adding an effective amount of a second antibody specific for an epitope on a metallic cation-first type of naturally occurring polypeptide complex to the first antigen-antibody complex to form a second antigen-antibody complex, wherein the second antibody does not substantially cross-react with an epitope found on the first type of naturally occurring polypeptide alone; and determining the amount of the metallic cation in the body fluid by detecting the amount of the second antigen-antibody complex.

11. A kit for detecting a metallic cation in a sample of a body fluid from an animal, which comprises:

a first antibody specific for a naturally occurring polypeptide, wherein the polypeptide can bind to the metallic cation; and a second antibody specific for the metallic cation.

12. A kit according to claim 11, wherein the first antibody is immobilized on a substrate.

13. A kit according to claim 11, wherein the second antibody is labeled by a detectable agent.

14. A kit according to claim 11, wherein the first antibody is specific for an epitope of a metallic cation-naturally occurring polypeptide complex.

15. A kit according to claim 14, wherein the first antibody is specific for an epitope not found on the naturally occurring polypeptide alone.

16. A kit according to claim 15, wherein the first antibody does not substantially cross-react with an epitope found in the naturally occurring polypeptide alone.

17. A kit according to claim 11, wherein the metallic cation is a lead cation or a mercury cation.

18. A kit according to claim 11, wherein the first antibody is specific for a naturally occurring polypeptide selected from the group consisting of δ-aminolevulinic acid dehydratase (ALAD), hemoglobin, human serum albumin, transferrin, glutathione, and protein kinase C.

\* \* \* \* \*

UNITED STATES PATENT AND TRADEMARK OFFICE
CERTIFICATE OF CORRECTION

PATENT NO. : 5,532,136
DATED : July 2, 1996
INVENTOR(S) : Carlson, et al.

It is certified that error appears in the above-indentified patent and that said Letters Patent is hereby corrected as shown below:

Column 34, line 22, insert -- a -- after the word " for ".

Column 34, line 22, delete " is " after the word " cation ".

Signed and Sealed this

Twenty-first Day of January, 1997

Attest:

BRUCE LEHMAN

*Attesting Officer*     *Commissioner of Patents and Trademarks*